United States Patent
Ito et al.

(10) Patent No.: US 9,477,026 B2
(45) Date of Patent: Oct. 25, 2016

(54) LIGHT SOURCE SYSTEM HAVING A PLURALITY OF LIGHT SOURCE MODULES EACH HAVING AN IRRADIATION MODULE WITH LIGHT GUIDE

(71) Applicant: OLYMPUS CORPORATION, Tokyo (JP)

(72) Inventors: Takeshi Ito, Hino (JP); Eiji Yamamoto, Musashimurayama (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 95 days.

(21) Appl. No.: 14/294,696

(22) Filed: Jun. 3, 2014

(65) Prior Publication Data

US 2014/0286038 A1     Sep. 25, 2014

Related U.S. Application Data

(63) Continuation of application No. PCT/JP2012/082053, filed on Dec. 11, 2012.

(30) Foreign Application Priority Data

Dec. 13, 2011   (JP) ................................ 2011-272563

(51) Int. Cl.
*F21V 8/00* (2006.01)
*A61B 1/00* (2006.01)
(Continued)

(52) U.S. Cl.
CPC ......... *G02B 6/0008* (2013.01); *A61B 1/00167* (2013.01); *A61B 1/043* (2013.01);
(Continued)

(58) Field of Classification Search
CPC .... G02B 6/0026; G02B 6/04; G02B 6/0653; G02B 6/3825; G02B 6/0006; A61B 1/0653; A61B 1/00167
USPC ........................................................ 362/583
See application file for complete search history.

(56) References Cited

U.S. PATENT DOCUMENTS

| 8,908,740 B2 * | 12/2014 | Nagahama ........... A61B 1/0653 362/217.08 |
| 2008/0262316 A1 * | 10/2008 | Ajima .................. A61B 1/0669 600/178 |
| 2010/0254153 A1 | 10/2010 | Hama et al. |

FOREIGN PATENT DOCUMENTS

| JP | 61-68205 U | 5/1986 |
| JP | 3-49727 A | 3/1991 |

(Continued)

OTHER PUBLICATIONS

Japanese Office Action dated Aug. 4, 2015 in related Japanese Patent Application No. 2011-272563, together with English language translation.
International Search Report dated Feb. 12, 2013 issued in PCT/JP2012/082053.
English translation of International Preliminary Report on Patentability together with the Written Opinion dated Jun. 26, 2014 received in related International Application No. PCT/JP2012/082053.

*Primary Examiner* — Robert May
(74) *Attorney, Agent, or Firm* — Scully, Scott, Murphy & Presser, PC

(57) ABSTRACT

The light source system includes a plurality of light source modules configured to respectively emit light source lights having optical characteristics different from each other, and an irradiation module to which the light source modules are mechanically and detachably attached. The irradiation module includes a first light guide member, a second light guide member, and a first light conversion unit. The first light guide member has a central axis set in parallel with a central axis of the second light guide member. The first light conversion unit is optically connected to the first light guide member and is optically separated from the second light guide member.

42 Claims, 9 Drawing Sheets

(51) Int. Cl.
*A61B 1/04* (2006.01)
*F21V 9/16* (2006.01)
*F21V 19/04* (2006.01)
*F21Y 101/02* (2006.01)
*F21Y 113/00* (2016.01)

(52) U.S. Cl.
CPC .............. *F21V 9/16* (2013.01); *F21V 19/045* (2013.01); *F21V 2200/00* (2015.01); *F21Y 2101/02* (2013.01); *F21Y 2101/025* (2013.01); *F21Y 2113/005* (2013.01)

(56) References Cited

FOREIGN PATENT DOCUMENTS

| | | |
|---|---|---|
| JP | 8-136828 A | 5/1996 |
| JP | 10-225426 A | 8/1998 |
| JP | 10-243915 A | 9/1998 |
| JP | 10-337271 A | 12/1998 |
| JP | 2006-288534 A | 10/2006 |
| JP | 2008-258177 A | 10/2008 |
| JP | 2011-206227 A | 10/2011 |

* cited by examiner

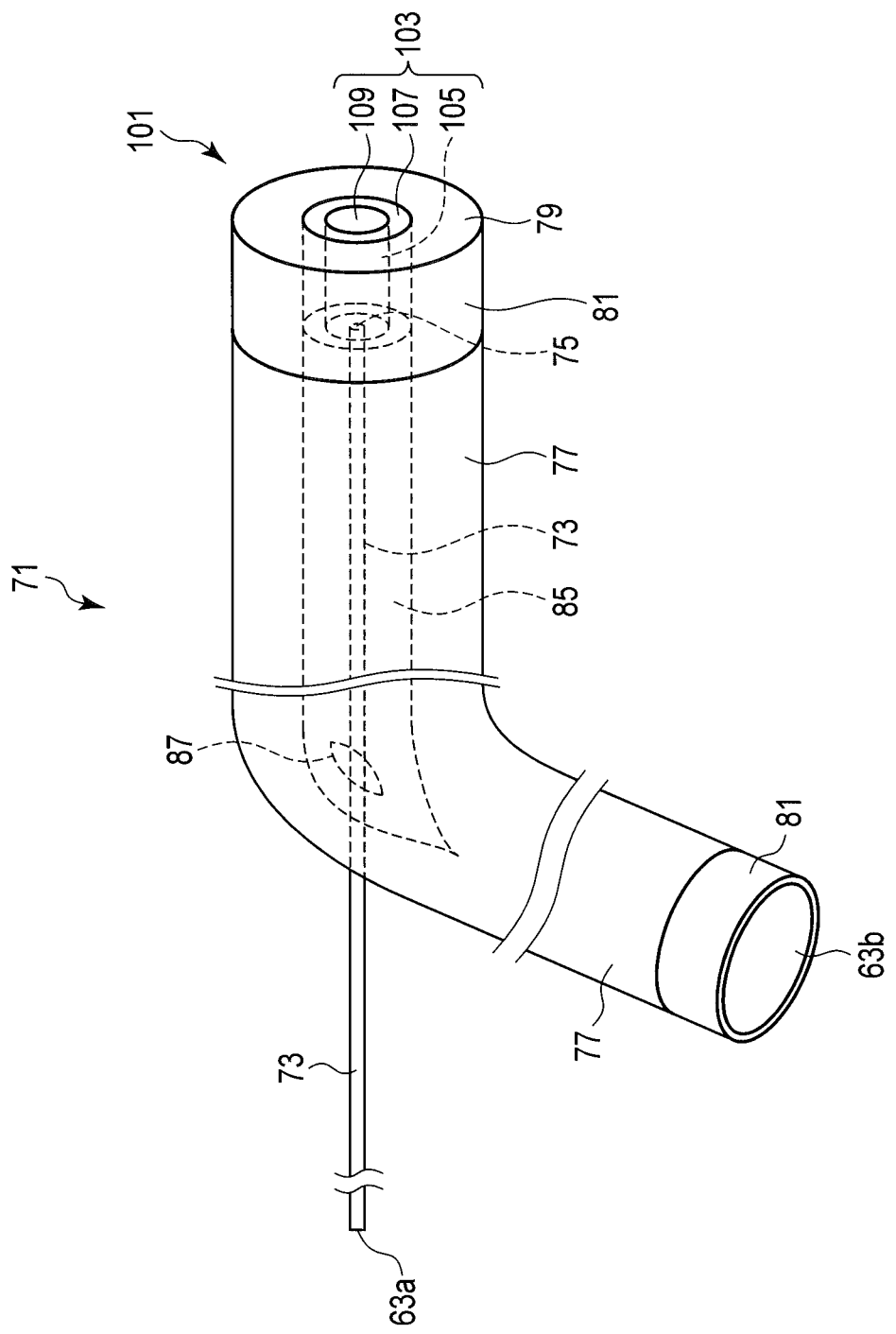
F I G. 4

US 9,477,026 B2

LIGHT SOURCE SYSTEM HAVING A PLURALITY OF LIGHT SOURCE MODULES EACH HAVING AN IRRADIATION MODULE WITH LIGHT GUIDE

CROSS-REFERENCE TO RELATED APPLICATIONS

This application is a Continuation Application of PCT Application No. PCT/JP2012/082053, filed Dec. 11, 2012 and based upon and claiming the benefit of priority from prior Japanese Patent Application No. 2011-272563, filed Dec. 13, 2011, the entire contents of all of which are incorporated herein by reference.

BACKGROUND OF THE INVENTION

1. Field of the Invention

The present invention relates to a light source system including a plurality of light guide members.

2. Description of the Related Art

For example, Jpn. Pat. Appln. KOKAI Publication No. 10-337271 discloses a light source system including a fluorescent endoscope. This light source system includes two types of light sources and two types of light guide members corresponding to the light sources and equipped on the fluorescent endoscope.

As the light sources, this light source system includes a laser light source for emitting laser beam, and a general illumination light source for emitting general illumination light. The laser beam and the general illumination light are used for irradiating biological tissues therewith. An image obtained by irradiating a biological tissue with the general illumination light and a fluorescent image obtained by irradiating the biological tissue with the laser beam are observed by a television camera through an image guide.

The fluorescent endoscope includes a first light guide member formed of an optical fiber for laser beam and configured to guide the laser beam from the laser light source to a distal end portion of the endoscope; a second light guide member formed of an optical fiber for general illumination light and configured to guide the general illumination light from the general illumination light source to the distal end portion of the endoscope; and a light conversion unit formed of a diffusion plate provided on the side of the distal end portion of the endoscope than the first light guide member and the second light guide member.

The optical fiber for general illumination light surrounds the optical fiber for laser beam in a close contact state. The light conversion unit is separated from the first light guide member and the second light guide member.

BRIEF SUMMARY OF THE INVENTION

An aspect of a light source system of the present invention includes a plurality of light source modules configured to respectively emit light source lights having optical characteristics different from each other; and an irradiation module to which the light source modules are mechanically and detachably attached, wherein the irradiation module includes a first light guide member configured to guide a light source light and having an optical characteristic in accordance with an optical characteristic of one of the light source lights, a second light guide member configured to guide a light source light and having an optical characteristic in accordance with an optical characteristic of another of the light source lights and different from the optical characteristic of the first light guide member, and a first light conversion unit configured to convert the optical characteristic of said one of the light source lights guided by the first light guide member and to emit this light source light as first converted light, wherein the first light guide member has a central axis set in parallel with a central axis of the second light guide member at near a side of the first light guide member where the first light conversion unit is arranged, and wherein the first light conversion unit is optically connected to the first light guide member and is optically separated from the second light guide member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a schematic perspective view showing a light guide unit and a first light conversion unit.

DETAILED DESCRIPTION OF THE INVENTION

An embodiment of the present invention will now be described in detail with reference to the accompanying drawings.

First Embodiment

Configuration

An explanation will be given of a first embodiment with reference to FIGS. 1, 2, 3A, 3B, 4, 5, and 6. It should be noted that some of the members are not illustrated in FIGS. 1, 2, 3A, 3B, 4, 5, and 6. Further, the light emitted from a light source 21a is called "light source light A", the light emitted from a light source 21b is called "light source light B", and the light emitted from a light source 21c is called "light source light C".

[Light Source System 10]

Figure 1:
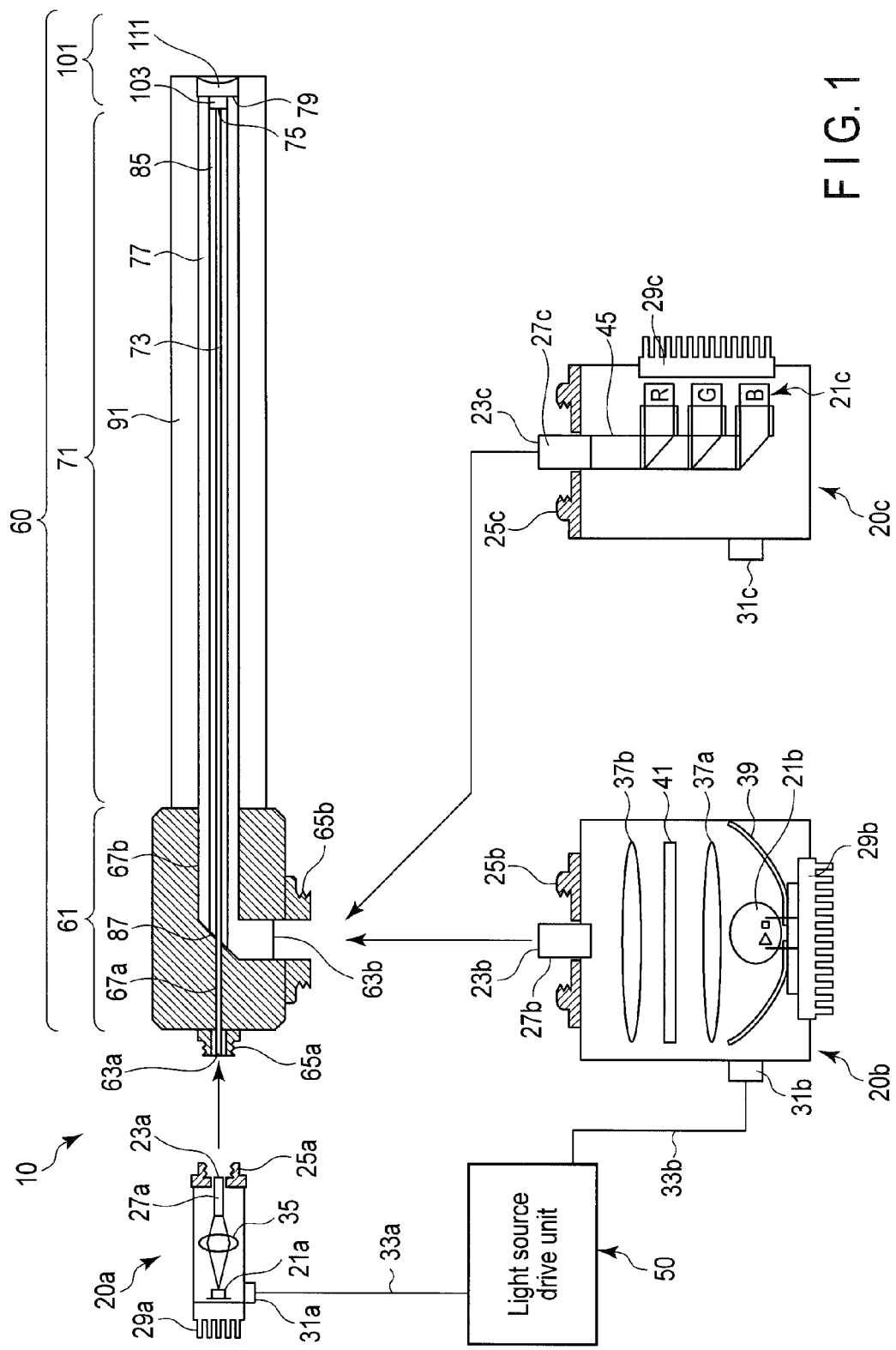
FIG. 1 is a schematic diagram showing a light source system according to a first embodiment of the present invention.

As shown in FIG. 1, a light source system 10 includes light source modules 20a, 20b, and 20c configured to respectively emit the light source lights A, B, and C having optical characteristics different from each other; a light source drive unit 50 configured to drive the light source modules 20a, 20b, and 20c; and an irradiation module 60 configured to irradiate an object to be observed with illumination light based on the light source lights A and B or C, wherein the light source modules 20a, 20b, and 20c are mechanically and detachably attached to the irradiation module 60.

The number of the light source modules is three, and there is one irradiation module 60. The single irradiation module 60 is shared by the three light source modules 20a, 20b, and 20c. This feature is also true of the light source drive unit 50. Since the three light source modules 20a, 20b, and 20c are provided relative to the irradiation module 60, the irradiation module 60 can emit illumination light in accordance with the purpose. The light source modules 20a, 20b, and 20c are respectively prepared as individual bodies. Further, the light source modules 20a, 20b, and 20c are prepared as bodies separated from the light source drive unit 50.

[Light Source Modules 20a, 20b, and 20c]

Next, an explanation will be given of common members having almost the same functions among the respective light source modules 20a, 20b, and 20c.

As shown in FIG. 1, the light source modules 20a, 20b, and 20c respectively include the light sources 21a, 21b, and 21c configured to respectively emit the light source lights A, B, and C; emission end portions 23a, 23b, and 23c configured to respectively emit the light source lights A, B, and C toward incident end portions 63a and 63b provided on the irradiation module 60; and connecting portions 25a, 25b, and 25c configured to connect the emission end portions 23a, 23b, and 23c to the incident end portions 63a and 63b, such that the incident end portions 63a and 63b are optically coupled with the emission end portions 23a, 23b, and 23c.

Further, as shown in FIG. 1, the light source modules 20a, 20b, and 20c respectively include light guide members 27a, 27b, and 27c configured to guide the light source lights A, B, and C emitted from the light sources 21a, 21b, and 21c to the emission end portions 23a, 23b, and 23c; and heat radiation mechanisms 29a, 29b, and 29c configured to release heat generated from the light source modules 20a, 20b, and 20c.

Further, as shown in FIG. 1, the light source modules 20a, 20b, and 20c respectively include electric terminals 31a, 31b, and 31c electrically connected to the light source drive unit 50 for driving the light sources 21a, 21b, and 21c, so as to receive control signals and electric power for causing the light sources 21a, 21b, and 21c to emit light. The electric terminals 31a, 31b, and 31c can be connected to connection cables 33a and 33b. The light sources 21a, 21b, and 21c are configured to be electrically connected to the light source drive unit 50 by the connection cables 33a and 33b.

[Light Source Module 20a]

As shown in FIG. 1, the light source module 20a further includes a lens 35 arranged between the light source 21a and the light guide member 27a and serving as a light condensing portion for condensing the light source light A emitted from the light source 21a onto the light guide member 27a.

For example, the light source 21a includes a blue semiconductor laser of, e.g., an InGaN-based type, which emits blue laser beam as the light source light A. The laser beam has a wavelength of, e.g., about 370 nm to about 500 nm. The light emitting point of the light source 21a is smaller than the light emitting points of the light sources 21b and 21c. Most of the laser beam is made incident onto the light guide member 27a by the lens 35.

For example, the light guide member 27a is formed of an optical fiber, arranged between the lens 35 and the emission end portion 23a, to guide the light source light A condensed by the lens 35 onto the emission end portion 23a. The light guide member 27a has an incident region smaller than those of the light guide members 27b and 27c described later.

The emission end portion 23a is arranged at the end portion of the light guide member 27a. The emission end portion 23a can be optically connected to the incident end portion 63a. The emission end portion 23a has an emission region smaller than those of the emission end portions 23b and 23c described later.

The connecting portion 25a is protruded while surrounding the emission end portion 23a and can be fitted to a connecting portion 65a provided on a connecting unit 61 described later. The connecting portion 25a is fitted to the connecting portion 65a, such that the emission end portion 23a is optically coupled with the incident end portion 63a, and the light source module 20a is mechanically connected to the irradiation module 60. In this way, the connecting portion 25a and the connecting portion 65a provide a function as a first connecting mechanism.

The heat radiation mechanism 29a releases heat generated from, e.g., the light source 21a. For example, the heat radiation mechanism 29a includes a Peltier element and a heat radiation fin.

[Light Source Module 20b]

As shown in FIG. 1, the light source module 20b further includes two lenses, 37a and 37b, arranged between the light source 21b and the emission end portion 23b and serving as light condensing portions for condensing the light source light B emitted forward from the light source 21b; a mirror 39 arranged behind the light source 21b to reflect forward that part of the light source light B, which is emitted backward from the light source 21b; and a filter 41 arranged between the two lenses 37a and 37b to cut unnecessary components from the light source light B.

In this respect, the "backward" corresponds to the rear side in the direction of travel of the light source light B, and the "forward" corresponds to the front side in the direction of travel of the light source light B.

For example, the light source 21b includes, e.g., a Xe lamp that emits lamp light as the light source light B. The lamp light is white light, for example. The Xe lamp is a type of discharge lamp and serves as a white light source. The light emitting point of the light source 21b is larger than the light emitting point of the light source 21a, and so the light source light B has a wide radiation angle, and the light source light B has a wide wavelength range.

The lens 37a disposed on the light source 21b side converts the light source light B emitted from the light source 21b into almost parallel light.

The mirror 39 includes a concave surface for condensing the light source light B onto the lens 37a.

The filter 41 cuts unnecessary ultraviolet components and infrared components from the light source light B. For example, the filter 41 is formed of a band pass filter or a combination of a low pass filter and a high pass filter.

The lens 37b arranged on the light guide member 27b side condenses the light source light B onto the light guide member 27b after unnecessary components are removed from the light source light B by the filter 41.

Part of the light source light B is emitted from the light source 21b toward the lens 37a. The other part of the light source light B is emitted from the light source 21b toward the mirror 39. This other part of the light source light B is reflected by the mirror 39 toward the lens 37a. Then, the light source light B is converted into parallel light by the lens 37a, then has its ultraviolet components and infrared components remove by the filter 41, and then is condensed and made incident onto the light guide member 27b by the lens 37b.

The light guide member 27b is formed of a light guide rod, arranged between the lens 37b and the emission end portion 23b, to guide the light source light B condensed by the lens 37b onto the emission end portion 23b. The light guide member 27b has an incident region larger than that of the light guide member 27a.

The emission end portion 23b is arranged at the end portion of the light guide member 27b. The emission end portion 23b can be optically connected to the incident end portion 63b. The emission end portion 23b has an emission region larger than that of the emission end portion 23a.

The connecting portion 25b is protruded while surrounding the emission end portion 23b and can be fitted to a connecting portion 65b provided on the connecting unit 61. The connecting portion 25b is fitted to the connecting portion 65b, such that the emission end portion 23b is optically coupled with the incident end portion 63b, and the light source module 20b is mechanically connected to the irradiation module 60. In this way, the connecting portion 25b and the connecting portion 65b provide a function as a second connecting mechanism.

For example, the heat radiation mechanism 29b includes a cooling fan and a heat radiation fin. The heat radiation mechanism 29b radiates heat generated from the light source 21b and heat of members caused by irradiation with the light source light B. These members include the mirror 39, for example.

[Light Source Module 20c]

As shown in FIG. 1, the light source module 20c further includes a combining optical system 45 arranged between the light source 21c and the light guide member 27c and configured to combine light.

For example, the light source 21c includes a red LED for emitting red LED light, a green LED for emitting green LED light, and a blue LED for emitting blue LED light. The light intensity of the red LED, the green LED, and the blue LED are respectively adjusted to generate LED light with one of various colors. For example, these kinds of LED light are combined at suitable ratios between them by the combining optical system 45 to generate white light (LED light) as the light source light C. The red LED, the green LED, and the blue LED are mounted on the same substrate, which is not shown. For example, this substrate is formed of at least one of substrates having high thermal conductivity, such as an aluminum substrate and an aluminum nitride substrate. The light emitting point of the light source 21c is larger than the light emitting point of the light source 21a, and so the light source light C has a wide radiation angle, and the light source light C has a wide wavelength range.

For example, the combining optical system 45 includes a dichroic mirror. The combining optical system 45 combines the red LED light, the green LED light, and the blue LED light to generate the light source light C. The combining optical system 45 condenses the light source light C onto the light guide member 27c.

The light guide member 27c is formed of a light guide rod, arranged between the combining optical system 45 and the emission end portion 23c, to guide the light source light condensed by the combining optical system 45 onto the emission end portion 23c. The light guide member 27c has an incident region larger than that of the light guide member 27a.

The emission end portion 23c is arranged at the end portion of the light guide member 27c. The emission end portion 23c can be optically connected to the incident end portion 63b. The emission end portion 23c has an emission region larger than that of the emission end portion 23a.

The connecting portion 25c is protruded while surrounding the emission end portion 23c and can be fitted to the connecting portion 65b provided on the connecting unit 61. The connecting portion 25c is fitted to the connecting portion 65b, such that the emission end portion 23c is optically coupled with the incident end portion 63b, and the light source module 20c is mechanically connected to the irradiation module 60. In this way, the connecting portion 25c and the connecting portion 65b provide a function as a second connecting mechanism.

The heat radiation mechanism 29c has almost the same structure as the heat radiation mechanism 29b. Accordingly, for example, the heat radiation mechanism 29c includes a cooling fan and a heat radiation fin. The heat radiation mechanism 29c radiates heat generated from the light source 21c and heat of members caused by irradiation with the light source light C. These members include the combining optical system 45, for example. The heat radiation mechanism 29c is mounted on the back side of a substrate, which is not shown.

The light source module 20c may include the lenses 37a and 37b and the filter 41.

The fundamental structure of the light source module 20c is almost the same as the fundamental structure of the light source module 20b, and so their structure and operation will be explained by use of the light source module 20b as an example.

[Light Source Drive Unit 50]

As shown in FIG. 1, the light source system 10 according to this embodiment includes the single light source drive unit 50, and this light source drive unit 50 is shared by the light source modules 20a, 20b, and 20c.

The light source drive unit 50 supplies electric power to the light source module 20a and the light source module 20b or the light source module 20c. Further, the light source drive unit 50 controls the light emitting state of the light source 21a and the light emitting state of the light source 21b or the light emitting state of the light source 21c. Accordingly, for example, the connection cable 33a is connected to the light source module 20a, and the connection cable 33b is connected to the light source module 20b or the light source module 20c.

The light source drive unit 50 includes a function for discriminating the types of the light source modules 20a, 20b, and 20c connected to the light source drive unit 50. Specifically, the connection cables 33a and 33b include electric power lines for supplying electric power to the light source modules 20a, 20b, and 20c, control signal lines for controlling the driving states of the light source modules 20a, 20b, and 20c, and discrimination signal lines for discriminating the types of the light source modules 20a, 20*b*, and 20*c* connected to the connection cables 33*a* and 33*b*. The light source drive unit 50 discriminates the types of the light source modules 20*a*, 20*b*, and 20*c* connected by the connection cables 33*a* and 33*b*, based on discrimination signals received via the discrimination signal lines. For example, where the light source drive unit 50 is connected to the light source module 20*a* by the connection cable 33*a*, the light source drive unit 50 detects a discrimination signal via the corresponding discrimination signal line. Then, the light source drive unit 50 supplies electric power and a control signal, in accordance with the light source 21*a* provided in the light source module 20*a*, to the light source module 20*a* via the corresponding electric power line and control signal line, respectively.

For example, a discrimination method for the light source modules 20*a*, 20*b*, and 20*c* may be adopted as follows: The light source modules 20*a*, 20*b*, and 20*c* respectively include memory devices, which are not shown, for recording the type information and drive information about the light source modules 20*a*, 20*b*, and 20*c*. The light source drive unit 50 reads these units of information via the connection cables 33*a* and 33*b* and thereby discriminates the light source modules 20*a*, 20*b*, and 20*c*.

Another discrimination method may be adopted as follows: The electric terminal 31*a* has a specific shape different from those of the electric terminals 31*b* and 31*c*, and the connection cable 33*a* includes a detection part for detecting this shape upon connection to the electric terminal 31*a*. This feature is also true of the electric terminals 31*b* and 31*c* in association with the connection cable 33*b*. The light source drive unit 50 discriminates the types of the light source modules 20*a*, 20*b*, and 20*c* based on such detection results.

Still another discrimination method may be adopted as follows: When the light source modules 20*a*, 20*b*, and 20*c* make connection to the light source drive unit 50 through the connection cables 33*a* and 33*b*, the light source modules 20*a*, 20*b*, and 20*c* respectively output electric signal patterns representing the light source modules 20*a*, 20*b*, and 20*c* to the light source drive unit 50 via the discrimination signal lines. The light source drive unit 50 discriminates the light source modules 20*a*, 20*b*, and 20*c* based on the electric signal patterns.

At this time, it is preferable that the light source drive unit 50 can adjust the setting of the light source modules 20*a*, 20*b*, and 20*c*, as desired, in accordance with not only the types of the light source modules 20*a*, 20*b*, and 20*c*, but also the type of the irradiation module 60 to be connected to the light source modules 20*a*, 20*b*, and 20*c*. In order to realize this, the irradiation module 60 needs to transmit information about the type of the irradiation module 60 to the light source drive unit 50. In this respect, the irradiation module 60 may transmit information about the irradiation module 60 to the light source drive unit 50 via the light source modules 20*a*, 20*b*, and 20*c* and the connection cables 33*a* and 33*b*, or it may transmit the information to the light source drive unit 50 via direct connection made between the light source drive unit 50 and the connecting unit 61.

[Irradiation Module 60]

As shown in FIG. 1, the irradiation module 60 includes the connecting unit 61 to be optically and mechanically connected to the light source module 20*a* and the light source module 20*b* or the light source module 20*c*; and a light guide unit 71 connected to the connecting unit 61 and configured to guide the light source lights A and B or C. The irradiation module 60 further includes a light conversion unit 101 provided at the end portion of the light guide unit 71 and configured to convert the light source lights A and B or C guided by the light guide unit 71 into illumination light and to emit the illumination light, or to emit light source light B or C directly outward as illumination light.

[Connecting Unit 61]

As shown in FIG. 1, the connecting unit 61 has an almost rectangular parallelepiped shape. The connecting unit 61 includes the incident end portion 63*a* and the connecting portion 65*a* both provided on a first plane; the incident end portion 63*b* and the connecting portion 65*b* both provided on a second plane orthogonal to the first plane; and a third plane opposite to the first plane and orthogonal to the second plane, the third plane being connected to the light guide unit 71.

The incident end portion 63*a* is a portion onto which the light source light A (blue laser beam) emitted from the emission end portion 23*a* is made incident. The incident end portion 63*a* is formed as an incident region smaller than that of the incident end portion 63*b* described later. The incident end portion 63*a* is arranged coaxially with the emission end portion 23*a*.

The connecting portion 65*a* is protruded from the first plane while surrounding the incident end portion 63*a* and can be fitted to the connecting portion 25*a*. The connecting portion 65*a* cannot be fitted to either the connecting portion 25*b* or the connecting portion 25*c*.

The incident end portion 63*b* is a portion onto which the light source light B (lamp light) emitted from the emission end portion 23*b* or the light source light C (LED light) emitted from the emission end portion 23*c* is made incident. The incident end portion 63*b* is formed as an incident region larger than that of the incident end portion 63*a*. The incident end portion 63*b* is arranged coaxially with the emission end portion 23*b* or the emission end portion 23*c*.

The connecting portion 65*b* is protruded from the second plane while surrounding the incident end portion 63*b* and can be fitted to the connecting portion 25*b* or the connecting portion 25*c*. The connecting portion 65*b* cannot be fitted to the connecting portion 25*a*.

The connecting unit 61 includes a hole portion 67*a* to which a light guide member 73 (described later) provided to the light guide unit 71 is fitted or bonded, and a hole portion 67*b* to which a light guide member 77 provided to the light guide unit 71 is fitted or bonded. The hole portions 67*a* and 67*b* are formed inside the connecting unit 61.

The hole portion 67*b* is formed bent from the second plane toward the third plane. The hole portion 67*b* connects to the outside at the second plane and the third plane. The hole portion 67*b* is larger in diameter than the hole portion 67*a*. The hole portion 67*a* is formed linearly from the first plane toward the third plane. The hole portion 67*a* connects to the outside at the first plane, and connects to the hole portion 67*b* at the third plane side.

[Light Guide Unit 71]

As shown in FIG. 1, the light guide unit 71 includes the light guide member 73 functioning as, e.g., a first light guide member for guiding the light source light A (laser beam) incident through the incident end portion 63*a*; the light guide member 77 functioning as, e.g., a second light guide member for guiding the light source light B or C (lamp light or LED light) incident through the incident end portion 63*b*; and an outer coat 91 made of resin and covering the light guide member 77. The light guide member 73 has optical characteristics corresponding to the optical characteristics of the light source light A incident through the incident end portion 63*a*. The light guide member 77 has optical characteristics corresponding to the optical characteristics of the light source light B or C incident through the incident end portion 63b. The optical characteristics of the light guide member 77 are different from the optical characteristics of the light guide member 73.

[Light Guide Member 73]

Figure 2:
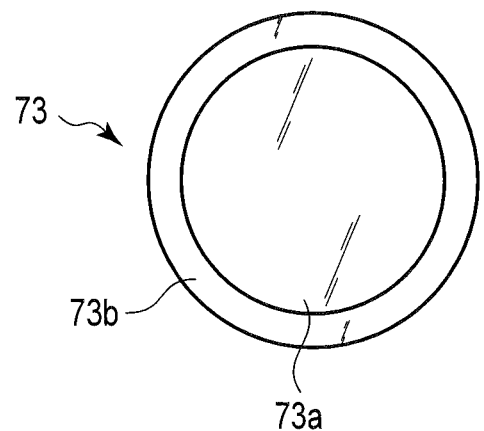
FIG. 2 is a front view showing a light guide member 73.

As shown in FIGS. 1 and 2, the light guide member 73 includes a single line optical fiber suitable for guiding the light source light A. The light guide member 73 is held by a ferrule, which is not shown, near the light guide member 73. The light guide member 73 includes a core 73a having a circular shape and a clad 73b covering the core 73a and having a refractive index lower than the refractive index of the core 73a. For example, the core 73a has a diameter of several µm to 200 µm. For illumination, the light guide member 73 is preferably formed of a multimode optical fiber. The light guide member 73 has a circular column shape.

Figure 5:
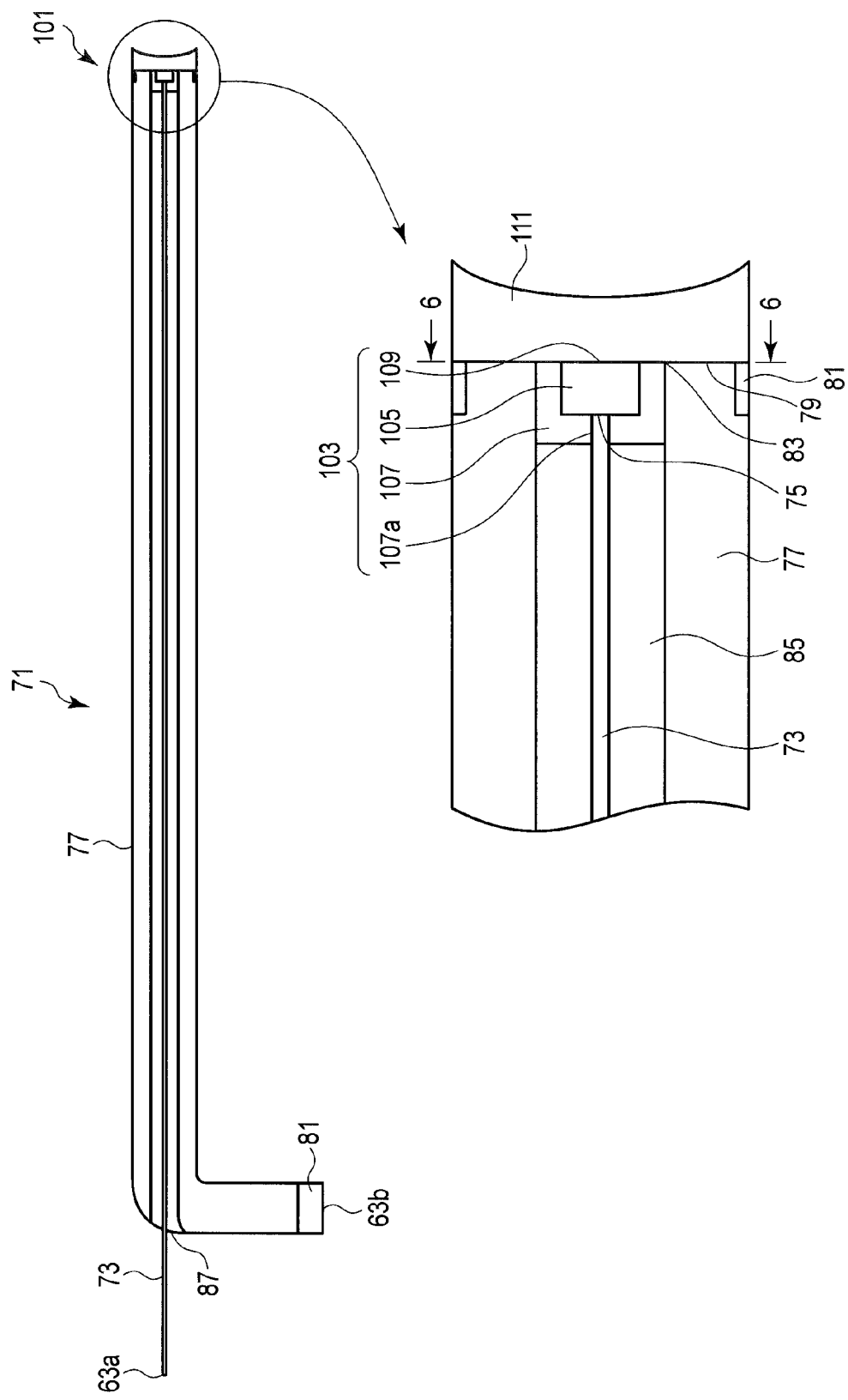
FIG. 5 is a view showing the structures of the light guide unit and a light conversion unit.

As shown in FIGS. 1, 4, and 5, one end portion of the core 73a representing one end portion of the light guide member 73 functions as the incident end portion 63a onto which the light source light A is made incident. Further, as shown in FIGS. 1, 4, and 5, the other end portion of the core 73a representing the other end portion of the light guide member 73 functions as the emission end portion 75 from which the light source light A is emitted. Thus, the light guide member 73 includes the emission end portion 75 (the other end portion) as a first emission end portion for emitting the light source light A. The emission end portion 75 is formed as an emission region smaller than that of the emission end portion 79 described later. The emission end portion 75 is provided on a first plane orthogonal to the central axis of the light guide member 73.

As shown in FIGS. 1, 4, and 5, the light guide member 73 (incident end portion 63a) is arranged coaxially with the light guide member 27a (emission end portion 23a). The light guide member 73 is arranged to be linear in the connecting unit 61. The one end portion of the light guide member 73 is held by the connecting portion 65a. The light guide member 73 is fitted or bonded to the hole portion 67a at the connecting unit 61.

Further, for example, as shown in FIGS. 1, 4, and 5, the light guide member 73 is extended from the connecting unit 61 and is linearly arranged from the connecting unit 61 to the light conversion unit 101. The light guide member 73 arranged from the connecting unit 61 to the light conversion unit 101 is covered and protected by the light guide member 77, although the details will be described later. The other end portion (emission end portion 75) of the light guide member 73 is optically connected to a first light conversion unit 103 provided in the light conversion unit 101.

[Light Guide Member 77]

Figure 3A:
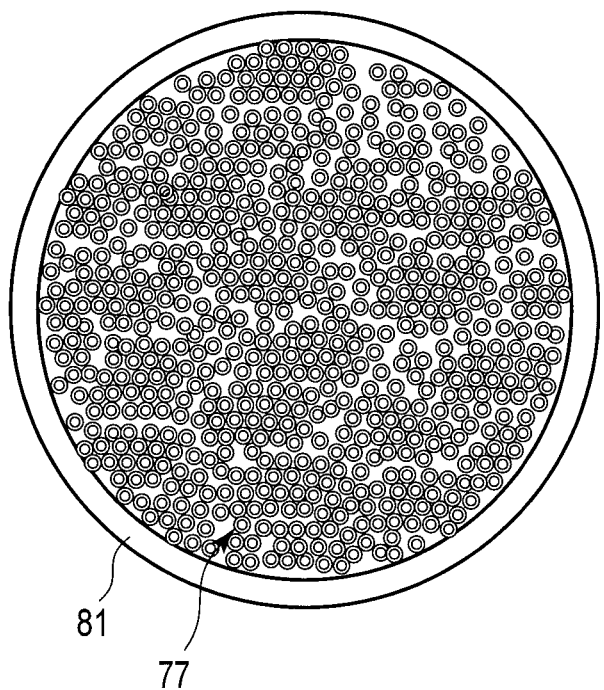
FIG. 3A is a front view showing a light guide member 77, viewed from its incident end portion side.

As shown in FIG. 3A, the light guide member 77 includes a bundle fiber formed of a plurality of optical fiber strands bundled together. Such a light guide member 77 is formed of, e.g., a so-called light guide. For example, the number of these optical fibers is several hundred to several thousand. As shown in FIGS. 1, 4, and 5, the light guide member 77 is thicker than the light guide member 73.

As shown in FIGS. 1, 4, and 5, one end portion of the light guide member 77 functions as the incident end portion 63b onto which the light source light B or the light source light C is made incident. Further, the other end portion of the light guide member 77 functions as the emission end portion 79 from which the light source light B or the light source light C is emitted. Thus, the light guide member 77 includes the emission end portion 79 (the other end portion) as a second emission end portion for emitting the light source light B or the light source light C. The emission end portion 79 is formed as an emission region larger than that of the emission end portion 75. The emission end portion 79 is provided on a second plane orthogonal to the central axis of the light guide member 77. The second plane is present on the same plane as the first plane on which the emission end portion 75 is provided, or is present more distantly from the light source module as compared with the first plane.

As shown in FIGS. 4 and 5, the one end portion of the light guide member 77 has the optical fibers arranged in a bundled state inside a casing 81 having a circular cylindrical shape. This feature is also true of the other end portion. Further, the one end portion has the optical fibers in a state of being fixed to each other by, e.g., an adhesive, and has them further fixed to the inner peripheral surface of the casing 81. This feature is also true of the other end portion. In other words, the both ends of the light guide member 77 are formed as fixed ends, and the fibers are freely movable with respect to each other, without being bonded, between the one end portion and the other end portion. For example, the casing 81 is made of a metal.

As shown in FIG. 1, since the incident end portion 63b is provided on the second plane orthogonal to both of the first plane and the third plane, the one end portion of the light guide member 77 is bent inside the connecting unit 61. The one end portion of the light guide member 77 is thus bent and held along with the casing 81 by the connecting portion 65b. The light guide member 77, in this state, is fitted or bonded to the hole portion 67b at the connecting unit 61. The one end portion (incident end portion 63b) of the light guide member 77 is arranged coaxially with the light guide member 27b (emission end portion 23b) or the light guide member 27c (emission end portion 23c).

Further, as shown in FIG. 1, the light guide member 77 is extended from the connecting unit 61 and is linearly arranged from the connecting unit 61 to the light conversion unit 101. The light guide member 77 arranged from the connecting unit 61 to the light conversion unit 101 is covered and protected by the outer coat 91. As shown in FIGS. 4 and 5, the other end portion (emission end portion 79) of the light guide member 77 is optically separated from the first light conversion unit 103 and is optically connected to a second light conversion unit 111 provided in the light conversion unit 101.

As shown in FIG. 3A, the one end portion (incident end portion 63b) of the light guide member 77 has the optical fibers arranged all over to form a circular shape. This one end portion is larger than the core 73a. This one end portion has a diameter of several hundred µm to 3 mm, in consideration of a property for efficiently receiving the light source light B or C, a property for inserting the one end portion into the hole portion 67b, and a property for inserting and disposing the illumination unit inside another member.

Figure 3B:
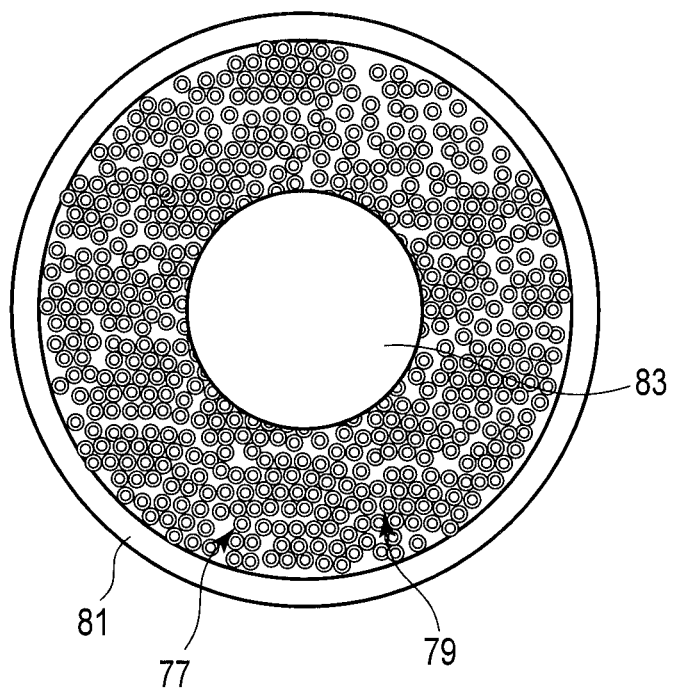
FIG. 3B is a front view showing the light guide member 77, viewed from its emission end portion side.

As shown in FIGS. 3B, 4, and 5, the other end portion (emission end portion 79) of the light guide member 77 has the optical fibers arranged biased to the outer edge side to form a ring shape. Accordingly, the other end portion includes an opening end portion 83 having a circular shape. The opening end portion 83 is arranged on the central axis of the light guide member 77. The opening end portion 83 is linearly continuous inside the light guide member 77, from the emission end portion 79 to the root of the bent portion of the light guide member 77. Accordingly, as shown in FIGS. 1 and 5, the light guide member 77 includes therein a cavity portion 85 having a circular column shape, and thus the light guide member 77 consequently has a circular cylindrical shape. The cavity portion 85 connects to the outside at the other end portion through the opening end portion 83. Further, the cavity portion 85 connects to the hole portion 67a at the connecting unit 61, and so a side surface opening portion 87 is formed at the root of the bent portion of the light guide member 77. The side surface opening portion 87 is arranged inside the hole portion 67b. The light guide member 73 is arranged through the cavity portion 85 and on the central axis of the cavity portion 85. The diameter of the cavity portion 85 is larger than the diameter of the light guide member 73. The optical fiber strands are bundled such that the cavity portion 85 formed inside the light guide member 77, the cavity portion 85 is used to arrange the light guide member 73 inside the light guide member 77. The light guide member 73 is arranged inside the light guide member 77 to be covered by the light guide member 77, such that the light guide member 77 covers the light guide member 73 to hold and protect the light guide member 73. The light guide member 73 and the light guide member 77 are arranged coaxially with each other in the light guide unit 71.

The emission end portion 79 has a ring shape representing a region defined by subtracting the opening end portion 83 from the other end portion.

[Assembling Procedure 1 of Light Guide Members 73 and 77]

The other end portion (emission end portion 75) of the light guide member 73 is connected to a spectral conversion member 105 of the first light conversion unit 103, in advance. The light guide member 77 is formed in advance by bundling a plurality of optical fibers (strands), such that the cavity portion 85 is formed inside. Thus, the light guide member 77 has a circular cylindrical shape.

Then, the light guide member 73 is inserted into the cavity portion 85 through the opening end portion 83.

Then, the light guide members 73 and 77 are connected to the connecting unit 61, as follows: The one end portion of the light guide member 77 is bent, and the side surface opening portion 87 is formed, such that the one end portion of the light guide member 73 is protruded from the side surface opening portion 87. The one end portion of the light guide member 73 is fitted or bonded to the hole portion 67a and is thereby held by the connecting portion 65a. The one end portion of the light guide member 77 is fitted or bonded to the hole portion 67b and is thereby held by the connecting portion 65b.

[Relationship Between Optical Characteristics of Light Guide Member 73 and Optical Characteristics of Light Guide Member 77]

The light guide member 73 has a light transmittance for blue laser beam within a wavelength region of about 370 nm to about 500 nm to guide the light source light A (blue laser beam). The numerical aperture NA of the light guide member 73 does not need to be larger than the numerical aperture NA of the light guide member 77.

Since the light guide member 77 guides the light source light B or C (lamp light or LED light), the numerical aperture NA of the light guide member 77 is selected to be larger than the numerical aperture NA of the light guide member 73. Further, in order to guide the light source light B or C, the light guide member 77 preferably has a wavelength transmission characteristic that is relatively flat for light of from the visible region to the near-infrared region. Further, the light guide member 77 is not required to have as high a transmittance for the light source light C (blue region light), which has relatively low visibility, as for light in the other wavelength regions.

When the optical characteristics of the light guide member 73 and the optical characteristics of the light guide member 77 are compared with each other, the following matters are noted.

A: It is preferable that the effective incident region (incident end portion 63b) of the light guide member 77 is larger than the effective incident region (incident end portion 63a) of the light guide member 73.

B: It is preferable that the numerical aperture of the light guide member 77 is larger than the numerical aperture of the light guide member 73.

C: It is preferable that, for blue region light, the transmittance of the light guide member 73 is larger than the transmittance of the light guide member 77.

In this embodiment, since the light source 21a emits blue laser beam, "C" set out above is prescribed for "blue region light". Accordingly, if the light source 21a emits laser beam having a desired color, it is prescribed for "desired color region", or "the peak wavelength of the light source light A guided by the light guide member 73", in other words.

Thus, it is preferable that, for the peak wavelength of the light source light A guided by the light guide member 73, the transmittance of the light guide member 73 is larger than the transmittance of the light guide member 77.

[Light Conversion Unit 101]

The light conversion unit 101 emits illumination light based on the light source lights A and B or C. This light conversion unit 101 includes the first light conversion unit 103 and the second light conversion unit 111.

[First Light Conversion Unit 103]

As shown in FIGS. 1 and 5, the first light conversion unit 103 is optically connected to the other end portion (emission end portion 75) of the light guide member 73, so that the light source light A guided by the light guide member 73 is made incident onto the first light conversion unit 103. Further, the first light conversion unit 103 is optically separated from the light guide member 77, so that the light source light B or C (lamp light or LED light) guided by the light guide member 77 is not made incident onto the first light conversion unit 103.

The light source light B (lamp light) emitted by the light source 21b includes the same wavelength component as that of the light source light A (blue laser beam). Thus, the light source light B includes a blue component, which is absorbed by the spectral conversion member 105 of the first light conversion unit 103 described later and is converted into yellow fluorescence by the spectral conversion member 105. Accordingly, if the first light conversion unit 103 is optically connected to the light guide member 77, even when the first light conversion unit 103 is irradiated only with the light source light B, it comes to be irradiated with illumination light including yellow fluorescence. In order to avoid this problem, the first light conversion unit 103 is optically independent of the light guide member 77.

As shown in FIGS. 4 and 5, the first light conversion unit 103 includes the spectral conversion member 105 serving as a first light conversion member for converting the light source light A into first converted light and which has a circular column shape; a holding member 107 that holds the spectral conversion member 105; and an emission end portion 109 provided in the spectral conversion member 105 and serving as a third emission end portion for emitting the first converted light.

The first light conversion unit 103 converts the optical characteristics of the light source light A guided by the light guide member 73, and emits the light source light A as the first converted light. More specifically, the spectral conversion member 105 absorbs part of blue laser beam emitted from the light source 21a, which is a blue semiconductor laser, and guided by the light guide member 73. The spectral conversion member 105 converts this part into yellow fluorescence and emits it. Further, the spectral conversion member 105 converts the other part of the blue laser beam into scattering light and emits it. At this time, the spectral conversion member 105 converts, as desired, at least one of the peak wavelength, spectral shape, radiation angle, light distribution, and light intensity, which are included in the optical characteristics of the blue laser beam.

When the spectral conversion member 105 includes a wavelength conversion member configured to convert the peak wavelength, spectral shape, radiation angle, light distribution, and light intensity, the spectral conversion member 105 is formed of, e.g., resin or glass with fluorescent substance powder of YAG:Ce dispersed therein.

Further, the spectral conversion member 105 may include a radiation angle conversion member for converting the radiation angle and/or a light distribution conversion member for converting the light distribution.

In the following explanation, light generated by mixing yellow fluorescence and scattering light with each other is called mixture light. The thickness and shape of the spectral conversion member 105 and the particle diameter and density of the fluorescent substance powder can be used to adjust the ratio between the light intensity of the yellow fluorescence and the light intensity of the scattering light. Then, the ratio between the light intensity of the yellow fluorescence and the light intensity of the scattering light can be used to adjust the color of the mixture light. In this embodiment, the ratio between the light intensity of the yellow fluorescence and the light intensity of the scattering light is adjusted by use of the thickness and shape of the spectral conversion member 105 and the particle diameter and density of the fluorescent substance powder, so that the mixture light becomes white light.

For example, the holding member 107 has a circular column shape. The cross section of holding member 107 has a concave shape, and the spectral conversion member 105 is arranged inside the recessed portion of the holding member 107. The holding member 107 includes an opening portion 107a formed at the bottom of the holding member 107 and connecting to the recessed portion.

The holding member 107 is attached to the other end portion of the light guide member 73 by an attaching member, which is not shown, so that the light source light A passes through the opening portion 107a and is made incident onto the spectral conversion member 105, and the other end portion (emission end portion 75) of the light guide member 73 is optically connected to the spectral conversion member 105. The holding member 107 is attached to the other end portion of the light guide member 73 by use of at least one of a bonding mechanism and a mechanical fitting mechanism. The outer peripheral surface of the holding member 107 is bonded to the inner peripheral surface of the light guide member 77.

For example, the emission end portion 109 has a circular shape.

[Second Light Conversion Unit 111]

As shown in FIGS. 1 and 5, the second light conversion unit 111 is optically connected to the other end portion (emission end portion 79) of the light guide member 77, so that the light source light B or C (lamp light or LED light) emitted from the emission end portion 79 of the light guide member 77 is made incident onto the second light conversion unit 111. The second light conversion unit 111 includes a radiation angle conversion member configured to convert the radiation (irradiation) angle of the light source light B or C incident onto the second light conversion unit 111, as desired. The radiation angle conversion member is one type of light distribution conversion member for enlarging the radiation angle. For example, the radiation angle conversion member includes a single concave lens or a lens group formed by combining a plurality of lenses, to convert the radiation angle and/or the light distribution, as desired. The second light conversion unit 111 uses the radiation angle conversion member to convert only the radiation angle of the light source light B or C without substantially changing the peak wavelength and spectral shape of the light source light B or C. At this time, the radiation angle conversion member converts the radiation angle, which is one of the optical characteristics, of the light source light B or C, to convert the light source light B or C into illumination light as second converted light.

Further, the second light conversion unit 111 is optically connected to the emission end portion 109 of the first light conversion unit 103, so that the first converted light emitted from the emission end portion 109 of the first light conversion unit 103 is made incident onto the second light conversion unit 111. The second light conversion unit 111 converts at least one of the peak wavelength, spectral shape, radiation angle, light distribution, and light intensity, which are included in the optical characteristics of the first converted light, to convert the first converted light into the second converted light.

In this respect, it suffices if the second light conversion unit 111 converts at least one of the peak wavelength, spectral shape, radiation angle, and light intensity, which are included in the optical characteristics of the first converted light and the optical characteristics of the light source light B or C, to convert at least one of the light source light B or C and the first converted light into the second converted light. Then, the second light conversion unit 111 emits the second converted light as illumination light.

[Relationship 1 in Arrangement Between Light Guide Member 73, Light Guide Member 77, and First Light Conversion Unit 103]

Figure 6:
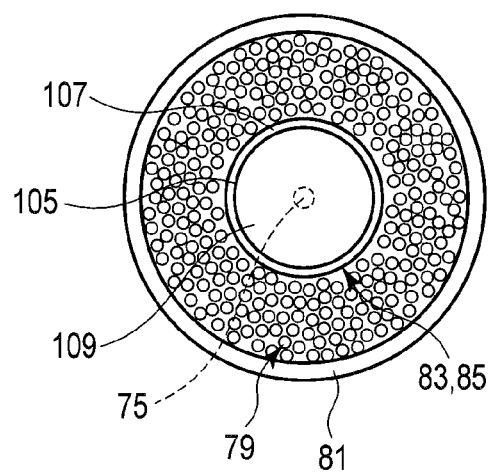
FIG. 6 is a front view showing the light guide unit, taken along a line 6-6 in FIG. 5.

As shown in FIGS. 5 and 6, the diameter of the other end portion (emission end portion 75) of the light guide member 73 is smaller than the diameter of the spectral conversion member 105. As described previously, the other end portion of the light guide member 73 is arranged in the cavity portion 85 (opening end portion 83) and is surrounded by the other end portion (emission end portion 79) of the light guide member 77. Accordingly, the first light conversion unit 103 is also arranged in the cavity portion 85 (opening end portion 83) and is surrounded by the other end portion of the light guide member 77.

The other end portion (emission end portion 75) of the light guide member 73, the other end portion (emission end portion 79) of the light guide member 77, and the first light conversion unit 103 are held in a collective state directly or indirectly by the casing 81 and the holding member 107, which serve as common holding members, and are fixed to the casing 81 and the holding member 107. The casing 81 and the holding member 107 prevent the other end portion (emission end portion 75) of the light guide member 73, the other end portion (emission end portion 79) of the light guide member 77, and the first light conversion unit 103 from separating from each other.

Further, the light guide member 73 and the light guide member 77 are fixed to each other at the emission end portion 75, which is the other end portion of the light guide member 73, and at the emission end portion 79, which is the other end portion of the light guide member 77. On the side toward the incident end portions 63a and 63b from these fixed portions, at least one part of the light guide member 73 on the one end portion side and at least one part of the light guide member 77 on the one end portion side are arranged as free ends, such that they are spatially movable or, in other words, three dimensionally.

The emission end portion 79, which is the other end portion of the light guide member 77, is arranged on the same plane as the emission end portion 109 of the spectral conversion member 105, i.e., farther away from the light source module 20a than the emission end portion 109, so that the light source light B or C emitted from the light guide member 77 is prevented from being shielded by the first light conversion unit 103, the first converted light emitted from the first light conversion unit 103 is prevented from being shielded by the light guide member 77, and the utilization efficiency of the light source light B or C and the first converted light is enhanced.

In this embodiment, the following are satisfied:

The central axis of the light guide member 73 corresponds to central axis of the core 73a, which is called a first central axis.

The central axis of the light guide member 77 corresponds to the central axis of the casing 81, which is called a second central axis.

As shown in FIG. 5, the first central axis is set in parallel with the second central axis at least near a side of the light guide member 73 where the first light conversion unit 103 is arranged. More specifically, the first central axis and the second central axis are arranged coaxially with each other between the opening end portion 83 and the side surface opening portion 87.

As shown in FIGS. 5 and 6, each of the emission end portion 75 and the emission end portion 109 has a circular shape, the emission end portion 79 has a ring shape, and the emission end portions 75, 79, and 109 are respectively arranged on concentric circles. Further, the outer edge of the emission end portion 79 has a circular shape. The spectral conversion member 105 has a circular column shape.

When the emission end portions 75, 79, and 109 are projected on a plane orthogonal to the central axis of the light guide member 73, the outer edge of the projection view of the emission end portion 75 formed on this plane is surrounded by the outer edge of the projection view of the emission end portion 109 formed on this plane. Further, the outer edge of the projection view of the emission end portion 109 is surrounded by the outer edge of the projection view of the emission end portion 79 formed on this plane. Thus, the emission end portion 75, the emission end portion 109, and the emission end portion 79 are arranged in this order outward from the center. The outer edges of the emission end portions 75, 79, and 109 are respectively arranged on concentric circles.

[Operation Method]

Next, an explanation will be given of an operation method according to this embodiment.

[Operation Method by Combination of Light Source Module 20a and Irradiation Module 60]

The light source module 20a is connected to the connecting unit 61 on the first plane and is connected to the light source drive unit 50 by the connection cable 33a. The light source drive unit 50 transmits a control signal to the light source module 20a via the connection cable 33a, and the light source 21a emits blue laser beam based on the control signal.

The laser beam is condensed by the lens 35 onto the light guide member 27a and thereby made incident onto the light guide member 27a, and is then guided by the light guide member 27a to the emission end portion 23a and emitted from the emission end portion 23a toward the incident end portion 63a. The laser beam is made incident onto the light guide member 73 from the incident end portion 63a, and is then guided by the light guide member 73 to the emission end portion 75 and emitted from the emission end portion 75 toward the first light conversion unit 103.

At the first light conversion unit 103, the spectral conversion member 105 is irradiated with the laser beam. Part of the laser beam is absorbed by the spectral conversion member 105 and is converted into yellow fluorescence by the spectral conversion member 105. Further, the other part of the laser beam is converted into blue scattering light by the spectral conversion member 105. The yellow fluorescence and the scattering light are emitted from the spectral conversion member 105 to the second light conversion unit 111. At this time, the yellow fluorescence and the scattering light are mixed and emitted as white light.

The radiation angle of the white light is enlarged by the radiation angle conversion member of the second light conversion unit 111, and then the white light is used as illumination light to irradiate an illumination target object therewith.

The light source 21a including the semiconductor laser can be more compact and save more power compared with the light source 21b including the Xe lamp and the light source 21c including the LEDs. Accordingly, the combination of the light source module 20a and the irradiation module 60 makes it possible to downsize the light source system 10 and to reduce the electric power for irradiation with the illumination light. Further, the laser beam can be made incident onto the light guide member 73 more efficiently than the lamp light and LED light. Accordingly, even with a small amount of electric power, it is possible to guide brighter light to the emission end portion 75 of the light guide member 73, so that the second light conversion unit 111 can efficiently generate brighter illumination light. Thus, the combination of the light source module 20a and the irradiation module 60 is effective in a case where the light source system 10 needs to be downsized, in a case where the electric power for the light source system 10 is limited, and/or in a case where more efficient brighter white light is required.

[Operation Method by Combination of Light Source Module 20b and Irradiation Module 60]

The light source module 20b is connected to the connecting unit 61 on the second plane and is connected to the light source drive unit 50 by the connection cable 33b. The light source drive unit 50 transmits a control signal to the light source module 20b via the connection cable 33b, and the light source 21b emits lamp light based on the control signal.

The lamp light is made incident onto the light guide member 27b, and is then guided by the light guide member 27b to the emission end portion 23b and emitted from the emission end portion 23b toward the incident end portion 63b. The lamp light is made incident onto the light guide member 77 from the incident end portion 63b, and is then guided by the light guide member 77 to the emission end portion 79 and emitted from the emission end portion 79 toward the second light conversion unit 111.

At the second light conversion unit 111, the radiation angle conversion member is irradiated with the lamp light. The radiation angle of the lamp light is enlarged by the radiation angle conversion member of the second light conversion unit 111, and then the lamp light is used as illumination light to irradiate an illumination target object therewith.

The lamp light emitted from the Xe lamp is white light having a spectrum relatively similar to sunlight. Thus, the combination of the light source module 20b and the irradiation module 60 is effective in a case where it irradiates an illumination target object with light approximate to sunlight.

[Operation Method by Combination of Light Source Module 20c and Irradiation Module 60]

The light source module 20c is used in place of the light source module 20b, and is connected to the connecting unit 61 on the second plane and is connected to the light source drive unit 50 by the connection cable 33b. The light source drive unit 50 transmits a control signal to the light source module 20c via the connection cable 33b, and the light source 21c emits LED light based on the control signal.

The operation of the LED light thereafter is almost the same as the operation of the lamp light.

The light source module 20c can emit LED light having various colors. Further, the light source module 20c is configured to combines the LED light having various colors by the combining optical system 45 and to emit the combined light. Thus, the combination of the light source module 20c and the irradiation module 60 is effective in a case where it is necessary to meet demands for the color of illumination light.

The light source 21c including the LEDs can be more compact and save more power compared with the light source 21b including the Xe lamp. Accordingly, the combination of the light source module 20c and the irradiation module 60 makes it possible to downsize the light source system 10 and to reduce the electric power for irradiation with the illumination light. Thus, the combination of the light source module 20c and the irradiation module 60 is effective in a case where the light source system 10 needs to be downsized, and/or in a case where the electric power for the light source system 10 is limited.

Further, the light source 21c including the LEDs can be turned on and off more quickly and can be modulated in brightness at a higher speed compared with the light source 21b including the Xe lamp. Thus, the combination of the light source module 20c and the irradiation module 60 is suitable for an application where the light source system 10 is readily started and stopped in use, without performing warm-up. Further, this combination is suitable for a usage application in which the brightness is modulated and/or turned on and off at a high speed.

Further, the LEDs have a longer service life than the Xe lamp and do not cause sudden breakdowns, so they can be stably used for a long time without maintenance.

[Effects]

As described above, according to this embodiment, the irradiation module 60 including the light guide members 73 and 77 further includes the light conversion unit 101 and is configured to be combined with the light source modules 20a, 20b, and 20c. In this embodiment, the light conversion unit 101 is configured such that the optical characteristics of the light source light A can be converted (adjusted) by the first light conversion unit 103 to match the optical characteristics of the light source light B or C.

Further, the first light conversion unit 103 is optically connected to the light guide member 73, and is optically separated from the light guide member 77, so that it is optically independent of the light guide member 77. Consequently, in this embodiment, the optical characteristics of the light source light B or C can be prevented from being converted by the first light conversion unit 103.

Thus, in this embodiment, as the optical characteristics can be adjusted to match each other, the light source system 10 can be shared for various purposes, without constructing individual dedicated systems in accordance with these purposes. Consequently, the light source system 10 can be cheaper, and the cost performance of the light source system 10 is thereby improved.

Specifically, in this embodiment, the irradiation module 60 is shared by the light source modules 20a, 20b, and 20c, and the single irradiation module 60 can emit various types of illumination light in accordance with the purpose. Accordingly, in this embodiment, the light source system 10 can be provided such that it can be shared for various purposes. Further, in this embodiment, the light source system 10 can be provided such that it can address various purposes without constructing individual systems dedicated to such purposes.

The optical characteristics of the light source lights mentioned here are, for example, the light distribution, color, and brightness of the light source lights. Further, the feature that the optical characteristics of the light source light A can be converted (adjusted) to match the optical characteristics of the light source light B or C means that part or all of the optical characteristics of the light source light A can be converted (adjusted) such that the observer hardly feels anything unnatural, for example.

Further, in this embodiment, the emission end portion 75, the emission end portion 79, and the first light conversion unit 103 are held in a collective state directly or indirectly by the casing 81 and the holding member 107, which serve as common holding members. In other words, the emission end portion 75, the emission end portion 79, and the first light conversion unit 103 are fixed to the same portion, i.e., the distal end portion of the light guide unit 71. Consequently, in this embodiment, the light source lights A and B or C can be emitted reliably from the same position, so that the user hardly feels anything unnatural in observation, even though the light source lights A and B or C are used. Further, in this embodiment, when the light source lights A and B or C are alternately turned on, it is possible to suppress differences therebetween in formation of shadows and so forth.

In this embodiment, for example, when the light source module 20a is combined with the irradiation module 60, it is possible to downsize the light source system 10, to effectively address the limit of the electric power for the light source system 10, and to efficiently realize bright white light.

In this embodiment, for example, when the light source module 20a is combined with the irradiation module 60, the operation of the first light conversion unit 103 varies depending on the wavelength of the laser beam.

For example, in the first light conversion unit 103, the spectral conversion member 105 containing fluorescent substance powder of YAG:Ce described previously absorbs blue laser beam and converts it into yellow fluorescence. At this time, the spectral conversion member 105 does not absorb or convert blue violet laser beam or laser beam with a wavelength longer than green.

However, the spectral conversion member 105 according to this embodiment functions as a radiation angle conversion member for converting the laser beam to enlarge its radiation angle, regardless of the wavelength of the laser beam. Accordingly, the spectral conversion member 105 emits white illumination light, while converting the wavelength of the blue laser beam and converting the radiation angle of the illumination light. Further, the spectral conversion member 105 emits the light while converting the radiation angle of blue violet laser beam or laser beam with a wavelength longer than green.

As described above, in this embodiment, even though the light guide member 73 uses the single line optical fiber, a plurality of types of illumination light can be emitted by use of a combination of the wavelength of the laser beam with the first light conversion unit 103.

Further, in this embodiment, for example, when the light source module 20b is combined with the irradiation module 60, it can irradiate an illumination target object with light approximate to sunlight.

Further, in this embodiment, the light guide member 77 is shared by the light sources 21b and 21c that respectively emit the lamp light and LED light. Consequently, in this embodiment, the number of light guide members 77 does not need to be equal to the number of the light sources 21b and 21c, thereby preventing an increase in the number of light guide members 77.

Further, in this embodiment, the light emitting region for the lamp light and the light emitting region for the LED light are larger than the light emitting region for the laser beam, and the optical characteristics of the lamp light and the optical characteristics of the LED light are similar to each other. Accordingly, in this embodiment, the light guide member 77 can be shared, and the bundle fiber can be used for the light guide member 77.

Further, in this embodiment, the second light conversion unit 111 converts only the radiation angle of the light source light B or C (lamp light or LED light), without substantially changing the peak wavelength or spectral shape of the light source light B or C. The lamp light or the LED light is used in this state to irradiate an illumination target object therewith. Accordingly, in this embodiment, the second light conversion unit 111 can also be shared for the light sources 21b and 21c.

Further, in this embodiment, the central axis of the light guide member 73 and the central axis of the light guide member 77 are arranged coaxially with each other. Consequently, in this embodiment, the center of the irradiation region used when the first converted light is converted and emitted by the second light conversion unit 111 agrees with the center of the irradiation region used when the lamp light or the LED light is converted and emitted by the second light conversion unit 111. Further, in this embodiment, the size and shadow formation of the irradiation region for the laser beam can be almost the same as the size and shadow formation of the irradiation region for the lamp light or the LED light. Accordingly, in this embodiment, when the light source lights A and B or C are switchingly used for irradiating an illumination target object, it is possible to alleviate an unnatural feeling of the observer, which is caused by the switching.

Particularly, in this embodiment, the emission end portion 75, the emission end portion 79, and the emission end portion 109 are respectively arranged on concentric circles, and so the irradiation region and shadow formation of the illumination light can be more constant.

Further, in this embodiment, the other end portion of the light guide member 77 is connected to the first light conversion unit 103, and so the irradiation region and shadow formation of the illumination light hardly shift even if the light guide unit 71 is bent.

Further, in this embodiment, the one end portion side of the light guide member 73 and the one end portion side of the light guide member 77 are arranged as free ends, so that they are movable relative to each other in the central axis direction of the light guide member 73. Consequently, in this embodiment, the light guide unit 71 can be easily bent, and the probability of the light guide members 73 and 77 being broken is low even if the light guide unit 71 is bent.

Further, in this embodiment, for example, the laser beam and the lamp light can be set by the second light conversion unit 111 to be the same in an optical characteristic (for example radiation angle). Further, in this embodiment, the second light conversion unit 111 is configured to convert the radiation angle, and so the first light conversion unit 103 does not need to have the function of converting the radiation angle, and thus the first light conversion unit 103 can be more compact.

Further, in this embodiment, the light guide member 73 includes the single line optical fiber, so that it can deal with the light source module 20a that emits the laser beam.

Further, in this embodiment, the light guide member 77 includes the bundle fiber formed of a plurality of optical fiber strands bundled together, so that it can deal with the light source module 20b that emits the lamp light, or the light source module 20c that emits the LED light.

Further, in this embodiment, the light guide member 73 is arranged inside the light guide member 77 by use of the cavity portion 85, and so the diameter of the irradiation module 60 can be smaller.

[Modifications]

Next, an explanation will be given of modifications according to this embodiment.

[Modification 1 Concerning Light Source Drive Unit 50; See FIG. 7]

In this embodiment, the light source drive unit 50 controls the light source module 20a via the connection cable 33a. Although not shown, however, the light source drive unit 50 may control the light source module 20a via the connection cable 33b, the light source module 20b, and the connecting unit 61. In this case, the connecting unit 61 is connected to the light source module 20a. Thus, the connecting unit 61 and the light source module 20a are equipped with electric connection terminals, which include transmission and reception terminals for transmitting and receiving control signals, and supply terminals for supplying electric power. These connection portions are preferably utilized for the discrimination signal concerning the type of the light source module 20a.

Figure 7:
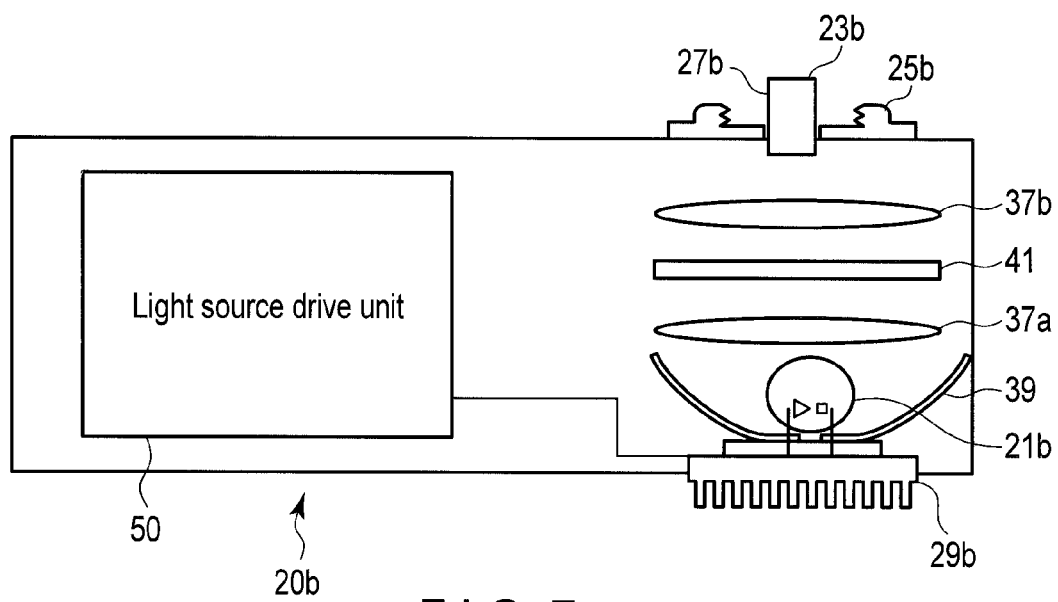
FIG. 7 is a schematic diagram showing a second light source module according to a modification 1.

Further, as shown in FIG. 7, the light source drive unit 50 may be directly equipped on the light source module 20b, which is larger in size and uses a larger amount of electric power, as compared with the light source module 20a. In this case, it is preferable that the light source drive unit 50 is connected to the connecting unit 61 and controls the light source module 20a via the connecting unit 61.

Further, the light source drive unit 50 may be directly equipped on the light source module 20a. In this case, the difference between the size of the light source module 20a and the size of the light source module 20b becomes smaller, and so the management for them, such as maintenance, can be easily performed.

[Modification 2 Concerning Assembly Procedure of Light Guide Members 73 and 77; See FIGS. 8, 9 and 10]

[Assembly Procedure 2 of Light Guide Members 73 and 77; See FIGS. 8 and 9]

Figure 8:
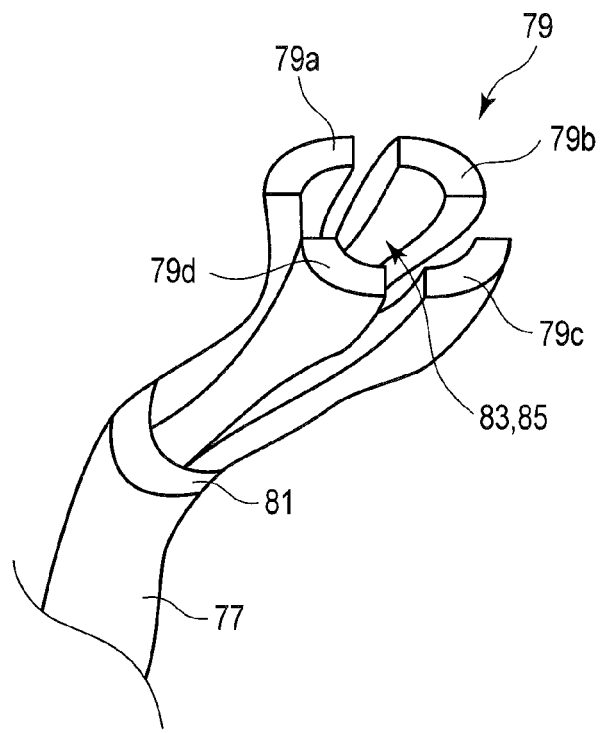
FIG. 8 is a perspective view showing the emission end portion side of a light guide member 77 according to a modification 2.
Figure 9:
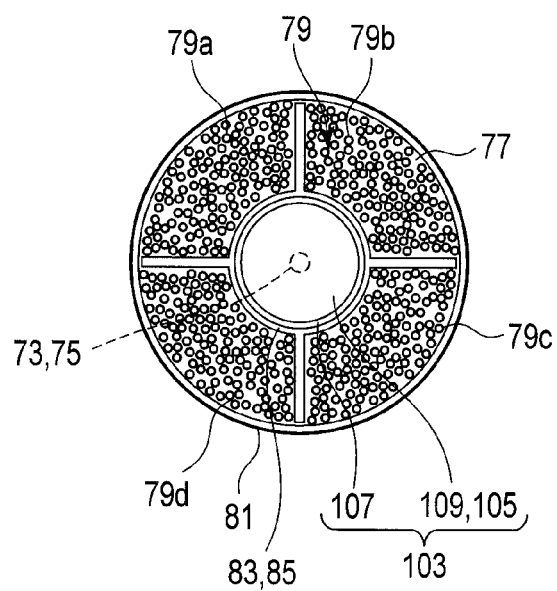
FIG. 9 is a front view showing the emission end portion of the light guide member 77 shown in FIG. 8.

The emission end portion 75 of the light guide member 73 is connected to the spectral conversion member 105, in advance. The light guide member 77 is formed in advance by bundling a plurality of optical fibers (strands), such that the cavity portion 85 is formed inside. Consequently, the light guide member 77 has a circular cylindrical shape. Further, at this time, as shown in FIGS. 8 and 9, the emission end portion 79 of the light guide member 77 is made such that the optical fiber strands are divided into a plurality of groups 79*a*, 79*b*, 79*c*, and 79*d*, and each of the groups 79*a*, 79*b*, 79*c*, and 79*d* is individually bundled and fixed. The groups 79*a*, 79*b*, 79*c*, and 79*d* are separated from each other, so that the emission end portion 79 is in an opened state.

The method for bundling and fixing each of the groups 79*a*, 79*b*, 79*c*, and 79*d* may be performed by use of various existing techniques. For example, an adhesive or the like may be used for binding the optical fiber strands.

Alternatively, an individual casing, which is not shown, may be used for bundling and fixing each of the groups 79*a*, 79*b*, 79*c*, and 79*d*.

Then, the light guide member 73 is inserted into the cavity portion 85 through the opening end portion 83.

Then, the emission end portion 79 is closed such that the respective groups 79*a*, 79*b*, 79*c*, and 79*d* surround the spectral conversion member 105 and fix the spectral conversion member 105.

Consequently, the light guide member 77 and the first light conversion unit 103 are accurately positioned and reliably fixed.

In this case, as shown in FIG. 8, it is preferable that the casing 81 is arranged in the side surface opening portion 87 than the other end portion (emission end portion 79), and more specifically at the root of the divided strands. In this case, the operation of fixing each of the groups to the spectral conversion member 105 can be more easily performed.

Although the number of the groups is four as an example, this number is not specifically limited and may be changed depending on the size of the first light conversion unit 103 and the thickness of the light guide member 77.

[Assembly Procedure 3 of Light Guide Members 73 and 77; See FIG. 10]

Figure 10:
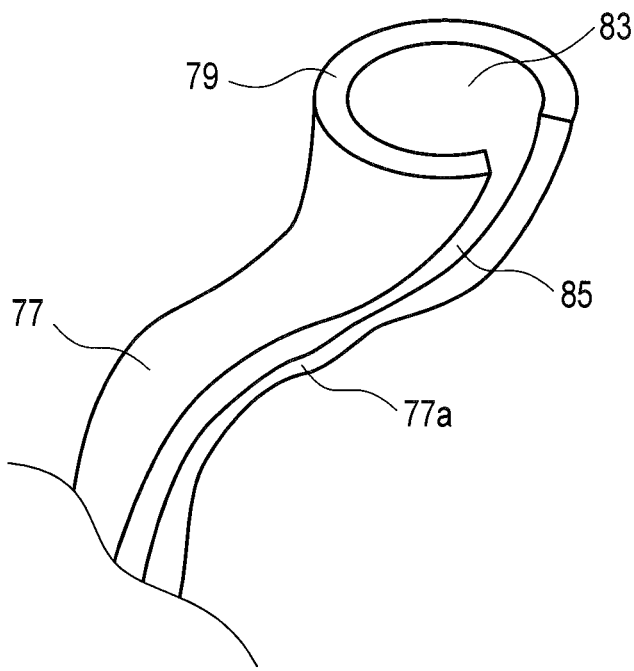
FIG. 10 is a perspective view showing the emission end portion side of a light guide member 77 according to a modification 2.

The emission end portion 75 of the light guide member 73 is connected to the spectral conversion member 105, in advance. As shown in FIG. 10, the light guide member 77 is formed in advance by bundling a plurality of optical fibers (strands), such that the cavity portion 85 is formed inside and that the light guide member 77 has a C-shaped cylindrical shape. Consequently, the light guide member 77 includes a notch portion 77*a* connecting to the cavity portion 85.

Then, the light guide member 73 is inserted into the cavity portion 85 through the notch portion 77*a*.

Consequently, the light guide member 77 and the first light conversion unit 103 are simply and accurately positioned and reliably fixed. Further, this assembly is effective when the light guide members 73 and 77 are short.

In this embodiment and this modification, the assembly procedure of the light guide members 73 and 77 is not limited to those described above. The assembly procedures described above are mere examples, and this structure can be realized by one of various methods, which are not explained here.

[Modification 3 about Light Guide Members 73 and 77]

In this embodiment, the light guide member 73 includes the single line optical fiber, and the light guide member 77 includes the bundle fiber formed of a plurality of optical fibers (strands) bundled together. However, this is not limiting.

For example, the light guide member 77 may be formed by patterning members having refractive indexes different from each other on a substrate or film. Alternatively, the light guide member 77 may be formed by arranging a light wave guide, which has been formed by layer-lamination and rolled to have a circular cylindrical shape, on a substrate or film.

The light guide member 73 may be formed of a light wave guide of the same type as the light guide member 77.

The light wave guide may be formed by separating or connecting a plurality of light guide members and patterning them into various complex light paths.

The light guide members 73 and 77 may be designed to have various optical characteristics, in accordance with the sizes of the light emitting regions of the light sources 21*a*, 21*b*, and 21*c* and/or in accordance with the purpose of using the light source system 10, without departing from the sprit of the present invention.

[Modification 4 of Light Conversion Unit 101]

In this embodiment, the first light conversion unit 103 is equipped with the spectral conversion member 105, and the second light conversion unit 111 is equipped with the radiation angle conversion member (one type of light distribution conversion member). However, this is not limiting. In this respect, other examples are shown below. The respective matters described below may be used in combination or may be used independently.

A: For example, the first and second light conversion units 103 and 111 may include at least one of a concave lens, convex lens, hologram lens, and diffraction grating. The concave lens or convex lens, or a combination of a concave lens and a convex lens, functions as a radiation angle conversion member for converting the radiation angle of illumination light. The hologram lens or diffraction grating functions as a radiation angle conversion member for converting the radiation angle of illumination light, or functions as a light distribution conversion member for converting the radiation direction of illumination light or the distribution of its light distribution part.

B: For example, in the first and second light conversion units 103 and 111, the radiation conversion member may be formed of resin or glass with particles dispersed inside. Alternatively, for example, the radiation angle conversion member may be formed by mixing a plurality of members, such as transparent particles, having refractive indexes different from each other. Each of these members, such as particles, is preferably made of a material having a high refractive index and a high reflection coefficient, such as alumina. Alternatively, for example, the radiation conversion member may be formed of a scattering plate, such as ground glass, or a diffusion plate having minute unevenness formed on the surface.

C: In the first and second light conversion units 103 and 111, the spectral conversion member 105 may include at least one of a light semiconductor material, SHG (secondary harmonic) material, and electroluminescent material.

D and E: The first and second light conversion units 103 and 111 may be made of a member that transmits part of the light source lights and shields other parts of the light source lights.

D: For example, this member is an optical filter having wavelength selectivity. For example, this optical filter may include at least one of a wavelength cut filter, color filter, and optical resonator (etalon).

E: For example, this member is a light transmission and modulation member having space selectivity. For example, the light transmission and modulation member may include at least one of a light switch, electrochromic, and liquid crystal device.

For example, in order to enhance the safety of the light source 21*a* and to remove speckles, "B" described above is preferably used. Further, when the radiation angles of the lamp light and the LED light are adjusted, at least one of "A" and "B" described above is preferably used.

[Modification 5 Concerning Relationship in Arrangement Between Light Guide Member 73, Light Guide Member 77, and First Light Conversion Unit 103]

[Relationship 2 in Arrangement Between Light Guide Member 73, Light Guide Member 77, and First Light Conversion Unit 103; See FIG. 11]

Figure 11:
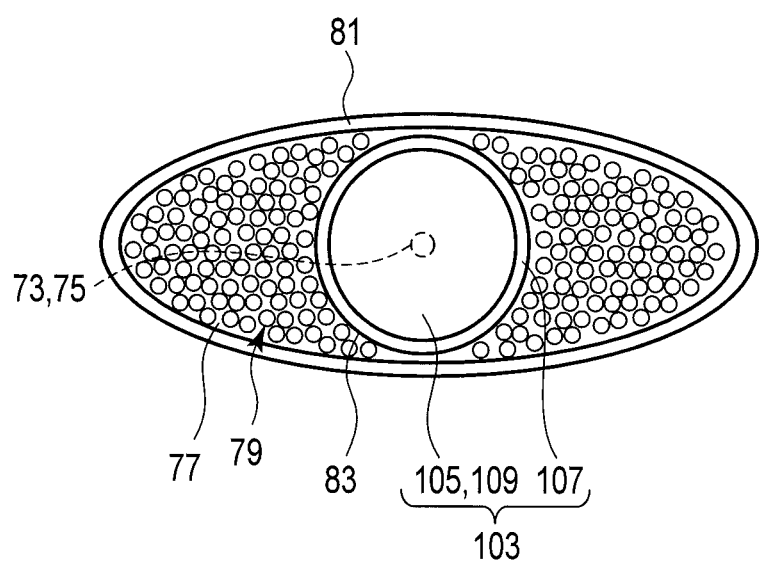
FIG. 11 is a front view showing a light guide unit according to a modification 5.

In this embodiment, the other end portion (emission end portion 79) of the light guide member 77 surrounding the first light conversion unit 103 has a ring shape. However, this is not limiting. As shown in FIG. 11, the other end portion (emission end portion 79) of the light guide member 77 may have an elliptic shape as its outline. In this modification, the outer edge of the emission end portion 79 surrounds the outer edge of the emission end portion 109.

The other end portion (emission end portion 79) of the light guide member 77 may have a shape other than the elliptic shape, which encompasses various shapes, such as a polygonal shape and crescent shape. More specifically, when the emission end portion 79 is projected on a plane orthogonal to the central axis of the light guide member 73, it suffices if the outer edge of the projection view of the emission end portion 79 formed on this plane has an elliptic shape or polygonal shape, or a composite shape of an elliptic shape and a polygonal shape. Accordingly, the other end portion (emission end portion 79) of the light guide member 77 may have an arbitrary shape, in accordance with the shape of a member to be equipped with the light guide member 77 and/or in accordance with the utilization purpose of the light guide member 77.

Consequently, in this modification, it is possible to improve the design flexibility and the layout flexibility at the distal end portion of the light guide unit 71.

Figure 12:
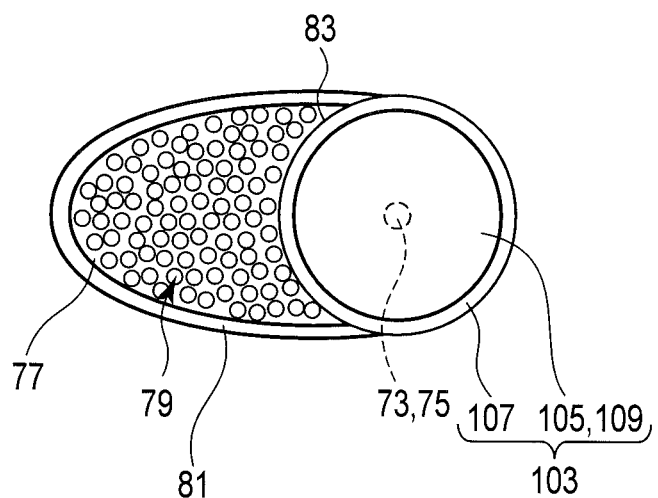
FIG. 12 is a front view showing a light guide unit according to a modification 5.

[Relationship 3 in Arrangement Between Light Guide Member 73, Light Guide Member 77, and First Light Conversion Unit 103; See FIG. 12]

In this embodiment, the light guide member 77 surrounds the entirety of the first light conversion unit 103. However, this is not limiting. For example, as long as the other end portion (emission end portion 79) of the light guide member 77 is arranged near the emission end portion 109 of the first light conversion unit 103, it suffices if the light guide member 77 surrounds at least one part of the first light conversion unit 103.

When the emission end portions 75, 79, and 109 are projected on a plane orthogonal to the central axis of the light guide member 73, the outer edge of the projection view of the emission end portion 75 formed on this plane is surrounded by the outer edge of the projection view of the emission end portion 109 formed on this plane. Further, at least one part of the outer edge of the projection view of the emission end portion 109 is substantially adjacent to at least one part of the outer edge of the projection view of the emission end portion 79 formed on this plane.

Specifically, the other end portion (emission end portion 79) of the light guide member 77 is attached to at least one part of the first light conversion unit 103 to surround at least one part of the first light conversion unit 103. The other end portion (emission end portion 79) of the light guide member 77 surrounds the emission end portion 109 of the spectral conversion member 105. Further, the thickness of the other end portion of the light guide member 77 varies depending on the position in the central axis direction of the light guide member 77.

Consequently, in this modification, it is possible to provide the light source system 10, such that it is compact and easily assembled and is improved in the design flexibility and the layout flexibility at the distal end portion of the light guide unit 71.

[Modification 6 Concerning First Light Conversion Unit 103]

In this embodiment, the spectral conversion member 105 is formed of, e.g., resin or glass with a fluorescent substance powder of YAG:Ce dispersed therein. However, this is not limiting, as long as white light can be generated from blue laser beam. For example, the spectral conversion member 105 may contain at least one of fluorescent substances that convert blue laser beam into white light when receiving the blue laser beam. Consequently, in this embodiment, it is possible to realize white light of a broader spectrum.

Further, the spectral conversion member 105 may contain a fluorescent substance that spectrally converts blue laser beam into a desired color. Consequently, in this embodiment, it is possible to emit illumination light having one of various colors other than white light. In relation to illumination light having one of various colors, it is possible to suitably select, as needed, whether to emit or not to emit diffused light of the laser beam outward.

[Modification 7 about Light Sources 21a, 21b, and 21c]

In this embodiment, the light source 21a includes the blue semiconductor laser. However, this is not limiting. It suffices if the light source 21a can be optically coupled with the light guide member 73 whose light emitting region and effective incident region are small. This light source 21a encompasses various laser light sources, such as a super luminescent diode (SLD) for emitting super luminescent light, for example.

Further, the light source 21a may include a laser light source for emitting laser beam having a color other than blue. For example, this laser light source encompasses a semiconductor laser, solid laser, and gas laser. At this time, when laser beam is emitted with its original color, a radiation conversion unit, such as a diffusion plate, may be provided.

Further, in this embodiment, the light source 21b includes the Xe lamp, and the light source 21c includes the LEDs. However, this is not limiting. It suffices if the light sources 21b and 21c can be optically coupled with the light guide member 77 whose light emitting region and effective incident region are large. For example, these light sources 21b and 21c may include a fluorescent tube or EL light emitting material.

Further, the light sources 21b and 21c may include a white laser or super-continuum light source. Further, the light source 21b may use one of various lamps, such as a discharge type lamp and filament type lamp. As the discharge type lamp, for example, a metal halide lamp may be utilized. As the filament type lamp, for example, a halogen lamp may be utilized.

Further, in this embodiment, the light source modules 20a, 20b, and 20c are respectively provided as bodies independent of each other. However, this is not limiting. For example, the light source module 20a and the light source module 20b may be integrated. In this case, for the connection of the light source modules 20a and 20b to the irradiation module 60, the two incident end portions 63a and 63b may be arranged on a single mechanically connecting portion 65a, or the connecting portions 65a and 65b may be arranged independently of each other.

The embodiment and the respective modifications described above are mere examples, and they can be further modified in various ways without departing from the sprit of the present invention.

Further, the present invention is not limited to the embodiment described above, as it is, but may be embodied along with some changes made in the structural elements without departing from their gist, in an implementation phase. Further, various inventions may be made by suitably combining a plurality of structure elements disclosed in the embodiment described above.

What is claimed is:

1. A light source system comprising:
a plurality of light source modules configured to respectively emit light source lights having optical characteristics different from each other; and
an irradiation module to which each of the plurality of light source modules is mechanically and detachably attached,
wherein the irradiation module includes:
a first light guide member configured to guide a light source light and having an optical characteristic in accordance with an optical characteristic of one of the light source lights,
a second light guide member configured to guide a light source light and having an optical characteristic in accordance with an optical characteristic of another of the light source lights and different from the optical characteristic of the first light guide member, and
a first light conversion unit configured to convert the optical characteristic of said one of the light source lights guided by the first light guide member and to emit this light source light as first converted light,
wherein the first light guide member has a central axis set in parallel with a central axis of the second light guide member near a side of the first light guide member where the first light conversion unit is arranged,
wherein the first light conversion unit is optically connected to the first light guide member and is optically separated from the second light guide member;
the first light guide member includes a first emission end portion configured to emit a light source light,
the second light guide member includes a second emission end portion configured to emit a light source light, and
the first emission end portion, the second emission end portion, and the first light conversion unit are held by a holding member in a collective state directly or indirectly; and
wherein the first light conversion unit includes a third emission end portion configured to emit the first converted light, and when the first emission end portion, the second emission end portion, and the third emission end portion are projected on a plane orthogonal to the central axis of the first light guide member, an outer edge of a projection view of the first emission end portion formed on the plane is surrounded by an outer edge of a projection view of the third emission end portion formed on the plane, and the outer edge of the projection view of the third emission end portion is surrounded by an outer edge of a projection view of the second emission end portion formed on the plane.

2. The light source system according to claim 1, wherein the first emission end portion has a circular shape, the second emission end portion has a ring shape, and the third emission end portion has a circular shape, and wherein the outer edges of the first emission end portion, the second emission end portion, and the third emission end portion are arranged on concentric circles.

3. The light source system according to claim 1, wherein the outer edge of the projection view of the second emission end portion has an elliptic shape, a polygonal shape, or a composite shape of an elliptic shape and a polygonal shape.

4. The light source system according to claim 1, wherein the first light guide member includes a single line optical fiber, and
the second light guide member includes a bundle fiber formed of a plurality of optical fiber strands bundled together.

5. The light source system according to claim 4, wherein the first light guide member and the second light guide member are fixed to each other at the first emission end portion and the second emission end portion, respectively, and
at least one part of the first light guide member and at least one part of the second light guide member are spatially movable with respect to each other on a side toward incident end portions from fixed portions.

6. The light source system according to claim 5, wherein the strands of the second light guide member are divided into a plurality of groups at the second emission end portion, and each of the groups is individually bundled and fixed.

7. The light source system according to claim 5, wherein the second light guide member is formed by bundling the plurality of optical fiber strands such that the second light guide member has a C-shaped cylindrical shape.

8. The light source system according to claim 1, wherein the first light conversion unit is configured to convert at least one of a peak wavelength, spectral shape, light distribution, and light intensity, which are included in the optical characteristic of said one of the light source lights.

9. The light source system according to claim 8, wherein the first light conversion unit includes a wavelength conversion member configured to convert the peak wavelength, the spectral shape, the light distribution, and the light intensity.

10. The light source system according to claim 8, wherein the first light conversion unit includes a light distribution member configured to convert the light distribution.

11. The light source system according to claim 1, wherein the light source light guided by the first light guide member includes laser beam or super luminescent light.

12. The light source system according to claim 11, wherein the laser beam includes blue region laser beam having a wavelength of 370 nm to 500 nm, and the first light conversion unit is configured to absorb part of the blue region laser beam, to convert the blue region laser beam into white light, and to emit the white light.

13. The light source system according to claim 1, wherein the light source light guided by the second light guide member includes lamp light or LED light.

14. The light source system according to claim 13, wherein the light source light guided by the second light guide member includes white light.

15. The light source system according to one of claim 1, wherein the irradiation module includes a plurality of connecting portions which can be independently fitted to each of the plurality of light source modules, and the plurality of connecting portions can be selectively fitted to each of the plurality of light source modules.

16. The light source system according to one of claim 1, wherein the irradiation module includes a plurality of connecting portions which can be independently fitted to each of the plurality of light source modules,
wherein the plurality of connecting portions include:
a first connecting portion configured to connect the first light guide member with one of the plurality of light source modules, and
a second connecting portion configured to connect the second light guide member with another of the plurality of light source modules,
wherein the first connecting portion and the second connecting portion are arranged on planes different from each other in the irradiation module.

17. The light source system according to claim 16, wherein a first plane on which the first connecting portion is arranged is orthogonal to a second plane on which the second connecting portion is arranged.

18. The light source system according to claim 16, wherein the first light guide member is arranged linearly to the first connecting portion, and the second light guide member is arranged in a bending manner to the second connecting portion.

19. The light source system according to claim 1, wherein the plurality of light source modules is configured as individual bodies; and
each of the plurality of light source modules is independently attached to the irradiation module.

20. A light source system comprising:
a plurality of light source modules configured to respectively emit light source lights having optical characteristics different from each other; and
an irradiation module to which each of the plurality of light source modules is mechanically and detachably attached,
wherein the irradiation module includes:
a first light guide member configured to guide a light source light and having an optical characteristic in accordance with an optical characteristic of one of the light source lights,
a second light guide member configured to guide a light source light and having an optical characteristic in accordance with an optical characteristic of another of the light source lights and different from the optical characteristic of the first light guide member, and
a first light conversion unit configured to convert the optical characteristic of said one of the light source lights guided by the first light guide member and to emit this light source light as first converted light at an emitting end of the first light conversion unit,
wherein the first light guide member has a central axis set in parallel with a central axis of the second light guide member near a side of the first light guide member where the first light conversion unit is arranged,
the first light conversion unit is optically connected to the first light guide member and is optically separated from the second light guide member,
the first light guide member includes a first emission end surface configured to emit a light source light,
the second light guide member includes a second emission end surface configured to emit a light source light,
the first emission end surface, the second emission end surface, and the first light conversion unit are held by a holding member in a collective state directly or indirectly;
a third emission end surface, which is disposed at the emitting end of the first light conversion unit and configured to emit the first converted light, is arranged on a first plane orthogonal to the central axis of the first light guide member,
the second emission end surface of the second light guide member is arranged on a second plane orthogonal to the central axis of the first light guide member, and
the second plane is present on a plane the same as the first plane or disposed at a location greater in distance from the light source modules than the first plane.

21. The light source system according to claim 20, wherein the second light guide member includes a bundle fiber formed by bundling a plurality of optical fiber strands, and
the second emission end surface is attached to at least one part of the first light conversion unit and surrounds at least one part of the first light conversion unit.

22. The light source system according to claim 21, wherein in the second light guide member including the second emission end surface, the strands are bundled such that cavity portion formed inside the second light guide member, cavity portion is used to arrange the first light guide inside the second light guide member.

23. The light source system according to claim 20, wherein the first light conversion unit is configured to convert at least one of a peak wavelength, spectral shape, light distribution, and light intensity, which are included in the optical characteristic of said one of the light source lights.

24. The light source system according to claim 20, wherein the light source light guided by the first light guide member includes laser beam or super luminescent light.

25. The light source system according to claim 20, wherein the light source light guided by the second light guide member includes lamp light or LED light.

26. The light source system according to claim 20, wherein the irradiation module includes a plurality of connecting portions which can be independently fitted to each of the plurality of light source modules, and the plurality of connecting portions can be selectively fitted to each of the plurality of light source modules.

27. The light source system according to claim 20, wherein the irradiation module includes a plurality of connecting portions which can be independently fitted to each of the plurality of light source modules,
wherein the plurality of connecting portions include:
a first connecting portion configured to connect the first light guide member with one of the plurality of light source modules, and
a second connecting portion configured to connect the second light guide member with another of the plurality of light source modules,
wherein the first connecting portion and the second connecting portion are arranged on planes different from each other in the irradiation module.

28. The light source system according to claim 20, wherein the plurality of light source modules is configured as individual bodies; and
each of the plurality of light source modules is independently attached to the irradiation module.

29. A light source system comprising:
a plurality of light source modules configured to respectively emit light source lights having optical characteristics different from each other; and
an irradiation module to which each of the plurality of light source modules is mechanically and detachably attached, wherein the irradiation module includes:
a first light guide member configured to guide a light source light and having an optical characteristic in accordance with an optical characteristic of one of the light source lights,
a second light guide member configured to guide a light source light and having an optical characteristic in accordance with an optical characteristic of another of the light source lights and different from the optical characteristic of the first light guide member, and
a first light conversion unit configured to convert the optical characteristic of said one of the light source lights guided by the first light guide member and to emit this light source light as first converted light,
wherein the first light guide member has a central axis set in parallel with a central axis of the second light guide member near a side of the first light guide member where the first light conversion unit is arranged,
the first light conversion unit is optically connected to the first light guide member and is optically separated from the second light guide member,
the first light guide member includes a first emission end portion configured to emit a light source light,
the second light guide member includes a second emission end portion configured to emit a light source light,
the first emission end portion, the second emission end portion, and the first light conversion unit are held by a holding member in a collective state directly or indirectly; and
the light source system further comprising a second light conversion unit optically connected to the second light guide member and the first light conversion unit, and the second light conversion unit is configured to convert at least one of a peak wavelength, spectral shape, light distribution, and light intensity, which are included in the optical characteristic of said another of the light source lights emitted from the second emission end portion and the optical characteristic of one of the first converted light emitted from the first light conversion unit, includes at least one lens configured to convert the light distribution, as desired and thereby to convert at least one of the light source light and the first converted light into a second converted light.

30. The light source system according to claim 29, wherein the first light conversion unit is configured to convert at least one of a peak wavelength, spectral shape, light distribution, and light intensity, which are included in the optical characteristic of said one of the light source lights.

31. The light source system according to claim 29, wherein the light source light guided by the first light guide member includes laser beam or super luminescent light.

32. The light source system according to claim 29, wherein the light source light guided by the second light guide member includes lamp light or LED light.

33. The light source system according to claim 29, wherein the irradiation module includes a plurality of connecting portions which can be independently fitted to each of the plurality of light source modules, and the plurality of connecting portions can be selectively fitted to each of the plurality of light source modules.

34. The light source system according to claim 29, wherein the irradiation module includes a plurality of connecting portions which can be independently fitted to each of the plurality of light source modules,
wherein the plurality of connecting portions include:
a first connecting portion configured to connect the first light guide member with one of the plurality of light source modules, and
a second connecting portion configured to connect the second light guide member with another of the plurality of light source modules,
wherein the first connecting portion and the second connecting portion are arranged on planes different from each other in the irradiation module.

35. The light source system according to claim 29, wherein the plurality of light source modules is configured as individual bodies; and
each of the plurality of light source modules is independently attached to the irradiation module.

36. A light source system comprising:
a plurality of light source modules configured to respectively emit light source lights having optical characteristics different from each other; and
an irradiation module to which each of the plurality of light source modules is mechanically and detachably attached,
wherein the irradiation module includes:
a first light guide member configured to guide a light source light and having an optical characteristic in accordance with an optical characteristic of one of the light source lights,
a second light guide member configured to guide a light source light and having an optical characteristic in accordance with an optical characteristic of another of the light source lights and different from the optical characteristic of the first light guide member, and
a first light conversion unit configured to convert the optical characteristic of said one of the light source lights guided by the first light guide member and to emit this light source light as first converted light,
wherein the first light guide member has a central axis set in parallel with a central axis of the second light guide member near a side of the first light guide member where the first light conversion unit is arranged,
the first light conversion unit is optically connected to the first light guide member and is optically separated from the second light guide member,
the first light guide member includes a first emission end portion configured to emit a light source light,
the second light guide member includes a second emission end portion configured to emit a light source light,
the first emission end portion, the second emission end portion, and the first light conversion unit are held by a holding member in a collective state directly or indirectly;
wherein the first light conversion unit includes a third emission end portion configured to emit the first converted light, and, when the first emission end portion, the second emission end portion, and the third emission end portion are projected on a plane orthogonal to the central axis of the first light guide member, an outer edge of a projection view of the first emission end portion formed on the plane is surrounded by an outer edge of a projection view of the third emission end portion formed on the plane, and the outer edge of the projection view of the third emission end portion is substantially adjacent to an outer edge of a projection view of the second emission end portion formed on the plane.

37. The light source system according to claim 36, wherein the first light conversion unit is configured to convert at least one of a peak wavelength, spectral shape, light distribution, and light intensity, which are included in the optical characteristic of said one of the light source lights.

38. The light source system according to claim 36, wherein the light source light guided by the first light guide member includes laser beam or super luminescent light.

39. The light source system according to claim 36, wherein the light source light guided by the second light guide member includes lamp light or LED light.

40. The light source system according to of claim 36, wherein the irradiation module includes a plurality of connecting portions which can be independently fitted to each of the plurality of light source modules, and the plurality of connecting portions can be selectively fitted to each of the plurality of light source modules.

41. The light source system according to claim 36, wherein the irradiation module includes a plurality of connecting portions which can be independently fitted to each of the plurality of light source modules, wherein the plurality of connecting portions include:

a first connecting portion configured to connect the first light guide member with one of the plurality of light source modules, and a second connecting portion configured to connect the second light guide member with another of the plurality of light source modules, wherein the first connecting portion and the second connecting portion are arranged on planes different from each other in the irradiation module.

42. The light source system according to claim 36, wherein the plurality of light source modules is configured as individual bodies; and each of the plurality of light source modules is independently attached to the irradiation module.

* * * * *